(12) United States Patent
Dynan et al.

(10) Patent No.: US 6,441,158 B1
(45) Date of Patent: Aug. 27, 2002

(54) OLIGOMERS THAT BIND TO KU PROTEIN

(75) Inventors: William S. Dynan; Sunghan Yoo, both of Augusta, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 0 days.

(21) Appl. No.: 09/223,139

(22) Filed: Dec. 30, 1998

Related U.S. Application Data

(60) Provisional application No. 60/070,278, filed on Dec. 31, 1997.

(51) Int. Cl.$^7$ ............................................... C07H 21/04
(52) U.S. Cl. ..................................... 536/24.5; 536/23.1
(58) Field of Search .......................... 435/6, 91.1, 325, 435/366; 536/23.1, 24.5; 514/44

(56) References Cited

U.S. PATENT DOCUMENTS

| | | | |
|---|---|---|---|
| 4,868,116 A | | 9/1989 | Morgan et al. |
| 4,980,286 A | | 12/1990 | Morgan et al. |
| 5,270,163 A | * | 12/1993 | Gold et al. ..................... 435/6 |
| 5,567,588 A | | 10/1996 | Gold et al. |

FOREIGN PATENT DOCUMENTS

| | | |
|---|---|---|
| WO | WO 89/07136 A2 | 8/1989 |
| WO | WO 90/02806 A1 | 3/1990 |
| WO | WO 91/19813 A | 12/1991 |
| WO | WO 95/23255 A2 | 8/1995 |

OTHER PUBLICATIONS

Cheng et al., Oligodeoxyribonucleotide length and sequence effects on intramolecular and intermolecular G–quartet formation, Gene, vol. 197, pp. 253–260, 1997.*
Stull et al., Antigene, ribozyme, and aptamer nucleic acid drugs: progress and prospects, Pharmaceutical Research, vol. 12 (4), pp. 465–483, 1995.*
Rojanasakul, Antisense Oligonucleotide therapeutics: drug delivery and targeting, Advanced Drug Delivery Reviews, vol. 18, pp. 115–131, 1996.*
Rathmell et al., Involvement of the Ku autoantigen in the cellular response to DNA double–strand breaks, Proc. Natl. Acad. Sci., vol. 91, pp. 7623–7627, Aug. 1994.*
Syvanen et al., Fast quantification of nucleic acid hybrids by affinity–based hybrid collection, NAR, vol. 14 (2), pp. 5037–5048, 1986.*
Kaczmarski et al., Lupus autoantigen ku protein binds HIV–TAR RNA in vitro, Biochem. Biophys. Res. Comm., vol. 196 (2), pp. 935–942, Oct. 1993.*
Jeggo et al., Sensitivity of chinese hamster ovary mutants defective in DNA double strand break repair to topoisomerase II inhibitors, Cancer Research, vol. 49, pp. 7057–7063, Dec. 1989.*
Acsadi, et al., "Human dystrophin expression in mdx mice after intramuscular injection of DNA constructs," Nature 352(6338):815–8 (1991).

Anderson, "DNA damage and the DNA–activated protein kinase," Trends Biochem Sci 18(11):433–7 (1993).

Bagshawe, "Towards generating cytotoxic agents at cancer sites," Br. J. Cancer 60:275–281 (1989).

Bagshawe, et al., "A cytotoxic agent can be generated selectively at cancer sites," Br. J. Cancer 58:700–703 (1988).

Banerji, et al., "A lymphocyte–specific cellular enhancer is located downstream of the joining region in immunoglobulin heavy chain genes," Cell 33(3):729–40 (1983).

Barrett, et al., "Selective enrichment and characterization of high affinity ligands from collections of random peptides on filamentous phage," Analytical Biochemistry 204:357–364 (1992).

(List continued on next page.)

Primary Examiner—Andrew Wang
(74) Attorney, Agent, or Firm—Kilpatrick Stockton LLP; Cynthia B. Rothschild; Charles W. Calkins

(57) ABSTRACT

Disclosed are oligomers that bind Ku protein. These oligomers are useful for inhibiting activation of DNA-PK, treating certain forms of autoimmune disease, detection and purification of Ku protein, and identification of proteins that interact with Ku protein. Preferably, the oligomers are composed of nucleotides, nucleotide analogs, or a combination. Most preferably, the oligomers are composed of ribonucleotides. Also disclosed is a method of inhibiting DNA repair, a method of identifying cellular proteins that interact with Ku protein, and a method of treating autoimmune disease in patients with anti-Ku antibodies. The disclosed oligomers can have several preferred features, either alone or in combination, in addition to Ku binding. One such feature, referred to herein as inhibition activity, is inhibition of DNA-PK kinase activity. Another preferred feature, referred to herein as aptamer motifs, is the presence of one or more of the base sequences GCUUUCCCANNNAC, A(A/C)AUGA, and AACUUCGA. These sequences— referred to herein as aptamer motif 1, aptamer motif 2, and aptamer motif 3, respectively—are associated with Ku binding capability. Another preferred feature, referred to herein as aptamer structure, is the presence of a structure similar to the structure shown in FIG. 6A. This structure has the general formula 5'-A-B-C-D-C'-E-A'-3', where A, B, C, D, C', E, and A' are components of the oligomer. In this structure, A and A' interact to form a stem structure, C and C' interact to form a stem structure, B and E make up a bulge region, and D is either a bulge or a loop. FIG. 6A depicts component D as a loop. Each of these preferred features (inhibition activity, aptamer motif, and aptamer structure) can be used either alone or in combination with one or both of the other characteristics.

8 Claims, 5 Drawing Sheets

OTHER PUBLICATIONS

Battelli, et al., "T lymphocyte killing by a xanthine–oxidase–containing immunotoxin," *Cancer Immunol. Immunother* 35:421–425 (1992).

Benseler, et al., "Hammerhead–like molecules containing non–nucleoside linkers are active RNA catalysts," *J. Am. Chem. Soc.* 115:8483–8484 (1993).

Berkner, et al., "Abundant expression of polyomavirus middle T antigen and dihydrofolate reductase in an adenovirus recombinant," *J Virol* 61(4):1213–20 (1987).

Blier, et al., "Binding of Ku protein to DNA. Measurement of affinity for ends and demonstration of binding to nicks," *J Biol Chem* 268(10):7594–601 (1993).

Bliss & Lane, "Ku selectively transfers between DNA molecules with homologous ends," *J Biol Chem* 272(9):5765–73 (1997).

Blunt, et al., "Defective DNA–dependent protein kinase activity is linked to V(D)J recombination and DNA repair defects associated with the murine scid mutation," *Cell* 80(5):813–23 (1995).

Boubnov, et al., "Complementation of the ionizing radiation sensitivity, DNA end binding, and V(D)J recombination defects of double–strand break repair mutants by the p86 Ku autoantigen," *Proc Natl Acad Sci U S A* 92(3):890–4 (1995).

Bout, et al., "Lung Gene Therapy: In Vivo Adenovirus–Mediated Gene Transfer to Rhesus Monkey Airway Epithelium," *Human Gene Therapy* 5:3–10 (1994).

Brown & Burlingham, "Penetration of host cell membranes by adenovirus 2," *J Virol* 12(2):386–96 (1973).

Brown & Greene, "Molecular and cellular mechanisms of receptor–mediated endocytosis," *DNA and Cell Biology* 10(6):399–409 (1991).

Caillaud, et al., "Adenoviral Vector as a Gene Delivery System into Cultured Rat Neuronal and Glial Cells" *Eur. J. Neuroscience* 5:1287–1291 (1993).

Cary, et al., "DNA looping by Ku an the DNA–dependent protein kinase," *Proc Natl Acad Sci U S A* 29 94(9):4267–72 (1997).

Cathala, "Use of n–butanol for efficient recovery of minute amounts of small RNA fragments and branched nucleotides from dilute solutions," *Nucleic Acids Res* 18(1):201 (1990).

Chardonnet & Dales, "Early Events in the Interaction of Adenoviruses with HeLa Cells: I. Penetration of Type 5 and Intracellular Release of the DNA Genome," *Virology* 40:462–477 (1970).

Chen & Gold, "Selection of high–affinity RNA ligands to reverse transcriptase: inhibition of cDNA synthesis and RNase H activity," *Biochemistry* 33(29):8746–56 (1994).

Clarenc, et al., "Delivery of antisense oligonucleotides by poly(L–lysine) conjugation and liposome encapsulation," *Anticancer Drug Des* 8(1):81–94 (1993).

Craft & Fatenejad, "Self antigens and epitope spreading in systemic autoimmunity," *Arthritis Rheum* 40(8):1374–82 (1997).

Crystal, "Transfer of Genes to Humans: Early Lesson and Obstacles to Success," *Science* 270:404–410 (1995).

Culver, et al., "In Vivo Gene Transfer with Retroviral Vector–Producer Cells for Treatment of Experimental Brain Tumors," *Science* 256:1550–1552 (1992).

Davidson & Hassell, "Overproduction of Polyomavirus Middle T Antigen in Mammalian Cells through the Use of an Adenovirus Vector," *J. Virology* 61:1226–1239 (1987).

Dvir, et al., "Ku autoantigen is the regulatory component of a template–associated protein kinase that phosphorylates RNA polymerase II," *Proc Natl Acad Sci U S A* 89(24):11920–4 (1992).

Dvir, et al., "Purification and characterization of a template-–associated protein kinase that phosphorylates RNA polymerase II," *J Biol Chem* 268(14):10440–7 (1993).

Falzon, et al., "EBP–80, a transcription factor closely resembling the human autoantigen Ku, recognizes single– to double–strand transitions in DNA," *J Biol Chem* 15 268(14):10546–52 (1993).

Felgner, "Particulate systems and polymers for in vitro and in vivo delivery of polynucleotides," *Advanced Drug Delivery Reviews*, 5:163–187 (1990).

Felgner & Ringold, "Lipofection: a highly efficient, lipid-–mediated DNA–transfection procedure," *Proc Natl Acad Sci U S A* 84(21):7413–7 (1987).

Felgner, et al., "Cationic liposome–mediated transfection," *Nature* 337(6205):387–8 (1989).

Fiers, et al., "Complete nucleotide sequence of SV40 DNA," *Nature* 273(5658):113–20 (1978).

Fowlkes & Shenk, "Transcriptional control regions of the adenovirus VAI RNA gene," *Cell* 22(2 Pt 2):405–13 (1980).

Fu, et al., "Hammerhead ribozymes containing non–nucleoside linkers are active RNA catalysts," *J. Am. Chem. Soc.* 116:4591–4598 (1994).

Getts & Stamato, "Absence of a Ku–like DNA end binding activity in the xrs double–strand DNA repair–deficient mutant," *J Biol Chem* 269(23):15981–4 (1994).

Giffin, et al., "Sequence–specific DNA binding and transcription factor phosphorylation by Ku Autoantigen/DNA–dependent protein kinase. Phosphorylation of Ser–527 of the rat glucocorticoid receptor," *J Biol Chem* 28 272(9):5647–58 (1997).

Giffin, et al., "Sequence–specific DNA binding by Ku autoantigen and its effects on transcription," *Nature* 380(6571):265–8 (1996).

Gold, et al., "Diversity of oligonucleotide functions," *Annu Rev Biochem* 64:763–97 (1995).

Gomez–Foix, et al., "Adenovirus–mediated Transfer of the Muscle Glycogen Phosphorylase Gene into Hepatocytes Confers Altered Regulation of Glycogen Metabolism," *J. Biol. Chem.* 267:25129–25134 (1992).

Good, et al., "Expression of small, therapeutic RNAs in human cell nuclei," *Gene Ther* 4(1):45–54 (1997).

Gottlieb & Jackson, "The DNA–dependent protein kinase: requirement for DNA ends and association with Ku antigen," *Cell* 72(1):131–42 (1993).

Greenaway, et al., "Human cytomegalovirus DNA: BamHI, EcoRI and PstI restriction endonuclease cleavage maps," *Gene* 18:355–360 (1982).

Guo, et al., "Direct fluorescence analysis of genetic polymorphisms by hybridization with oligonucleotide arrays on glass supports," *Nucleic Acids Res* 11 22(24):5456–65 (1994).

Gupta, et al., "Compilation of small RNA sequences," *Nucleic Acids Res.* 19:2073–2075 (1990).

Guzman, "Efficient Gene Transfer Into Myocardium by Direct Injection of Adenovirus Vectors" *Circulation Research* 73:1201–1207 (1993).

Haj–Ahmad et al., "Development of a Helper–Independent Human Adenovirus Vector and Its Use in the Transfer of the Herpes Simplex Virus Thymidine Kinase Gene" *J. Virology* 57:267–274 (1986).

Hall, et al., "Transcription initiation of eucaryotic transfer RNA genes," *Cell* 29(1):3–5 (1982).

He, et al., "Restoration of X–ray and etoposide resistance, Ku–end binding activity and V(D)J recombination to the chinese hamster sxi–3 mutant by hamster Ku86 cDNA," *Mutation Research* 363:43–56 (1996).

Hermanson, et al., eds., *Immobilized Affinity Ligands*, Craig T. Hermanson et al., eds. (Academic Press, New York, 1992).

Hoff,e t al., "Enhancer 1 binding factor, a Ku–related protein, is a positive regulator of RNA polymerase I transcription initiation," *Proc Natl Acad Sci U S A* 91(2):762–6 (1994).

Hughes, et al., "Monoclonal Antibody Targeting of Liposomes to Mouse Lung in Vivo" *Cancer Research*, 49:6214–6220, (1989).

Jaeger, et al., "Improved predictions of secondary structures for RNA," *Proc Natl Acad Sci U S A* 86(20):7706–10 (1989).

Jaeger, et al., "Predicting optimal and suboptimal secondary structure for RNA," *Methods Enzymol* 183:281–306 (1990).

Jin, et al., "Differential Etoposide Sensitivity of Cells Deficient in the Ku and DNA–PKcs Components of the DNA–dependent Protein Kinase" *Carcinogenesis* 19:965–97 (1998).

Johnstone, et al., *Immunochemistry In Practice* (Blackwell Scientific Publications, Oxford, England, 1987), on pp. 30–85.

Kaczmarski & Khan, "Lupus autoantigen Ku protein binds HIV–1 TAR RNA in vitro," *Biochem Biophys Res Commun* 196(2):935–42 (1993).

Kerkhof, "A comparison of substrates for quantifying the signal from a nonradiolabeled DNA probe," *Anal Biochem* 205(2):359–64 (1992.

Khrapko, et al., "[Hybridization of DNA with oligonucleotides immobilized in a gel: a convenient method for recording single base replacements]," *Mol Biol (Mosk)*— 25(3):718–30 (1991).

Kickhoefer, et al., "Vault ribonucleoprotein particles from rat and bullfrog contain a related small RNA that is transcribed by RNA polymerase III," *J Biol Chem* 268(11):7868–73 (1993).

Kim, et al., "Preparation of multivesicular liposomes," *Biochim Biophys Acta* 9 728(3):339–48 (1983).

Kirchgessner, et al., "DNA–dependent kinase (p350) as a candidate gene for the murine SCID defect," *Science* 267(5201):1178–83 (1995).

Kirshenbaum, "Highly efficient gene transfer into adult ventricular myocytes by recombinant adenovirus," *J. Clin. Invest.* 92:381–387 (1993).

Knuth, et al., "Purification and characterization of proximal sequence element–binding protein 1, a transcription activating protein related to Ku and TREF that binds the proximal sequence element of the human U1 promoter," *J Biol Chem* 265(29):17911–20 (1990).

Kuhn, et al., "DNA–dependent protein kinase: a potent inhibitor of transcription by RNA polymerase I," *Genes Dev* 9(2):193–203 (1995).

Kunkel & Pederson, "Transcription of a human U6 small nuclear RNA gene in vivo withstands deletion of intragenic sequences but not of an upstream TATATA box," *Nucleic Acids Res.* 18:7371–7379 (1989).

Kunkel, et al., "U6 small nuclear RNA is transcribed by RNA polymerase III," *Proc. Natl. Acad. Sci. USA* 83:8575–8579 (1987).

La Salle, et al., "An Adenovirus Vector for Gene Transfer into Neurons and Glia in the Brain," *Science* 259:988–990 (1993).

Labhart, "DNA–dependent protein kinase specifically represses promoter–directed transcription initiation by RNA polymerase I," *Proc Natl Acad Sci U S A* 28 92(7):2934–8 (1995).

Laimins, et al., "Osmotic control of kdp operon expression in *Escherichia coli,*" *Proc Natl Acad Sci U S A.* 78(1):464–8 (1981).

Langer, et al., "Enzymatic synthesis of biotin–labeled polynucleotides: novel nucleic acid affinity probes," *Proc Natl Acad Sci U S A* 78(11):6633–7 (1981).

Lee, et al., "Recognition of liposomes by cells: in vitro binding and endocytosis mediated by specific lipid headgroups and surface charge density," *Biochim Biophys Acta* 31 1103(2):185–97 (1992).

Lees–Miller, et al., "Absence of p350 subunit of DNA–activated protein kinase from a radiosensitive human cell line," *Science* 267(5201):1183–5 (1995).

Lees–Miller, et al., "Human DNA–activated protein kinase phosphorylates serines 15 and 37 in the amino–terminal transactivation domain of human p53," *Mol Cell Biol* 12(11):5041–9 (1992).

Letsinger & Wu, "Use of stilbenedicarbozamide bridge in stabilizing, monitoring, and photochemically altering folded conformations of oligonucleotides," *J. Am. Chem. Soc.* 117:7323–7328 (1995).

Litzinger & Huang, "Biodistribution and immunotargetability of ganglioside–stabilized dioleoylphosphatidylethanolamine liposomes," *Biochimica et Biophysica Acta* 1104:179–187 (1992).

Liu, et al., "Role of liposome size and RES blockade in controlling biodistribution and tumor uptake of GM1–containing liposomes," *Biochim Biophys Acta* 1104(1):95–101 (1992).

Lomant, et al., "Structural and energetic consequences of noncomplementary base oppositions in nucleic acid helices," *Prog Nucleic Acid Res Mol Biol* 15(0):185–218 (1975).

Ludwig, et al., "KU80 gene expression is Sp1–dependent and sensitive to CpG methylation within a novel cis element," *Gene* 199: 181–194 (1997).

Lusky, et al., "Bovine papilloma virus contains an activator of gene expression at the distal end of the early transcription unit," *Mol Cell Biol* 3(6):1108–22 (1983).

Massie, et al., "Construction of a Helper–Free Recombinant Adenovirus That Expresses Polyomavirus Large T Antigen" *Mol. Cell. Biol.* 6:2872–2883 (1986).

McConnell, et al., "The DNA–dependent protein kinase: a matter of life and (cell) death," *Curr Opin Cell Biol* 8(3):325–30 (1996).

Messier, et al., "p70 lupus autoantigen binds the enhancer of the T–cell receptor beta–chain gene," *Proc Natl Acad Sci U S A* 90(7):2685–9 (1993).

Mimori & Hardin, "Mechanism of interaction between Ku protein and DNA," *J Biol Chem* 261(22):10375–9 (1986).

Morsy, "Efficient Adenoviral–mediated Ornithine Transcarbamylase Expression in Deficient Mouse and Human Hepatocytes" *J. Clin. Invest.* 92:1580–1586 (1993).

Moullier, "Correction of lysosomal storage in the liver and spleen of MPS VII mice by implantation of genetically modified skin fibroblasts" *Nature Genetics* 4:154–159 (1993).

Mulligan, et al., "The Basic Science of Gene Therapy" *Science* 260:926–932 (1993).

Nielson, et al., "Transcription of human 5S rRNA genes is influenced by an upstream DNA sequence," *Nucleic Acids Res* 21(16):3631–6 (1993).

Noonberg, et al., "In vivo generation of highly abundant sequence–specific oligonucleotides for antisense and triplex gene regulation," *Nucleic Acids Res.* 22:2830–2836 (1995).

Okumura, et al., "Autoantigen Ku protein is involved in DNA binding proteins which recognize the U5 repressive element of human T–cell leukemia virus type I long terminal repeat," *FEBS Lett* 356(1):94–100 (1994).

Ortigao, et al., "Antisense effect of oligodeoxynucleotides with inverted terminal internucleotidic linkages: a minimal modification protecting against nucleolytic degradation," *Antisense Res Dev* 2(2):129–46 (1992).

Osborne, et al., "Transcription control region within the protein–coding portion of adenovirus E1A genes," *Mol Cell Biol* 4(7):1293–305 (1984).

Paillard & Strauss, "Analysis of the mechanism of interaction of simian Ku protein with DNA," *Nucleic Acids Res* 19(20):5619–24 (1991).

Pang, et al., "Ku proteins join DNA fragments as shown by atomic force microscopy," *Cancer Res* 57(8):1412–5 (1997).

Pease, et al., "Light–generated oligonucleotide arrays for rapid DNA sequence analysis," *Proc Natl Acad Sci U S A* 91(11):5022–6 (1994).

Peterson, et al., "Loss of the catalytic subunit of the DNA–dependent protein kinase in DNA double–strand–break–repair mutant mammalian cells," *Proc Natl Acad Sci U S A* 11 92(8):3171–4 (1995).

Petrak, "Design and Properties of particulate Carriers For Intravascular Administration," *Particulate Carrier*, (Ronald Allan, ed.) pp. 275–293, (1993).

Petrie, C.R., et al., "A Novel Biotinylated Adenylate Analogue Derived from Pyrazolo[3,4–d]pyrimidine for Labeling DNA Probes" *Bioconjugate Chem.* 2:441–446 (1991).

Pieles, et al., "Matrix–assisted laser desorption ionization time–of–flight mass spectrometry: a powerful tool for the mass and sequence analysis of natural and modified oligonucleotides," *Nucleic Acids Res* 11 21(14):3191–6 (1993).

Pietersz & McKenzie, "Antibody conjugates for the treatment of cancer," *Immunol Rev* 129:57–80 (1992).

Ragot, et al., "Replication–defective recombinant adenovirus expressing the Epstein–Barr virus (EBV) envelope glycoprotein gp340/220 induces protective immunity against EBV–induced lymphomas in the cottontop tamarin" *J. Gen. Virology* 74:501–507 (1993).

Ram, et al. "In Situ Retroviral–mediated Gene Transfer for the Treatment of Brain Tumors in Rats" *Cancel Res* 53:83–88 (1993).

Rathmell & Chu, "Involvement of the Ku autoantigen in the cellular response to DNA double–strand breaks," *Proc Natl Acad Sci U S A* 91(16):7623–7 (1994).

Reddy, et al., "The capped U6 small nuclear RNA is transcribed by RNA polymerase III," *J. Biol. Chem.* 262:75–81 (1987).

Reeves, et al., "Use of monoclonal antibodies for the characterization of novel DNA–binding proteins recognized by human autoimmune sera," *J Exp Med* 161(1):18–39 (1985).

Rich, et al., "Development and Analysis of Recombinant Adenoviruses for Gene Therapy of Cystic Fibrosis" *Human Gene Therapy* 4:461–476 (1993).

Roberts, et al., "A DNA–binding activity, TRAC, specific for the TRA element of the transferrin receptor gene copurifies with the Ku autoantigen," *Proc Natl Acad Sci U S A* 91(14):6354–8 (1994).

Roessler, "Adenoviral–mediated Gene Transfer to Rabbit Synovium In Vivo" *J. Clin. Invest.* 92:1085–1092 (1993).

Roffler, et al., "Anti–neoplastic glucuronide prodrug treatment of human tumor cells targeted with a monoclonal antibody–enzyme conjugate" *Biochemical Pharm.* 42:2062–2065 (1991).

Romero & Blackburn, "A conserved secondary structure for telomerase RNA," *Cell* 67(2):343–53 (1991).

Senter, et al., "Generation of Cytotoxic Agents by Targeted Enzymes," *Bioconjugate Chem.*, 4(1):3–9 (1993).

Senter, et al., "Generation of 5–fluorouracil from 5–fluorocytosine by monoclonal antibody–cytosine deaminase conjugates," *Bioconjug Chem* 2(6):447–51 (1991).

Seth, et al., "Evidence that the Penton Base of Adenovirus Is Involved in Potentiation of Toxicity of Pseudomonas Exotoxin Conjugated to Epidermal Growth Factor" *Mol. Cell. Biol.* 4:1528–1533 (1984).

Seth, et al., "Role of a low–pH environment in adenovirus enhancement of the toxicity of a Pseudomonas exotoxin–epidermal growth factor conjugate," *J. Virol.* 51:650–655 (1984).

Sinha, et al., "Polymer support oligonucleotide synthesis XVIII: use of beta–cyanoethyl–N,N–dialkylamino–/N–morpholino phosphoramidite of deoxynucleosides for the synthesis of DNA fragments simplifying deprotection and isolation of the final product," *Nucleic Acids Res* 12(11):4539–57 (1984).

Smider, et al., "Restoration of X–ray resistance and V(D)J recombination in mutant cells by Ku cDNA," *Science* 266(5183):288–91 (1994).

Smith & Steitz, "Sno storm in the nucleolus: new roles for myriad small RNPs," *Cell* 89(5):669–72 (1997).

Sproat, et al., "An efficient method for the isolation and purification of oligoribonucleotides," *Nucleosides and Nucleotides* 14:255–273 (1995).

Stimpson, et al., "Real–time detection of DNA hybridization and melting on oligonucleotide arrays by using optical wave guides," *Proc Natl Acad Sci U S A* 92(14):6379–83 (1995).

Sullenger, et al., "Expression of chimeric tRNA–driven antisense transcripts renders NIH 3T3 cells highly resistant to Moloney murine leukemia virus replication," *Mol Cell Biol* 10(12):6512–23 (1990).

Svensson, "Role of Vesicles During Adenovirus 2 Internalization into HeLa Cells" *J. Virology* 55:442–449 (1985).

Syvänen, et al., "Fast quantification of nucleic acid hybrids by affinity–based hybrid collection," *Nucleic Acids Res* 25 14(12):5037–48 (1986).

Szostak, "In Vitro genetics," *TIBS* 19:89, (1992).

Taccioli, et al., "Ku80: product of the XRCC5 gene and its role in DNA repair and V(D)J recombination," *Science* 265(5177):1442–5 (1994).

Thierry, et al., "Intracellular availability of unmodified, phosphorothioated and liposomally encapsulated oligodeoxynucleotides for antisense activity," *Nucleic Acids Res* 20(21):5691–8 (1992).

Thompson, et al., "Improved accumulation and activity of ribozymes expressed from a tRNA–based RNA polymerase III promoter," *Nucleic Acids Res* 23:2259–2268 (1995).

Topal & Fresco, "Complementary base pairing and the origin of substitution mutations," *Nature* 263(5575):285–9 (1976).

Tuerk & Gold, "Systematic evolution of ligands by exponential enrichment: RNA ligands to bacteriophage T4 DNA polymerase," *Science* 3 249(4968):505–10 (1990).

Usman, et al., "Automated chemical synthesis of long oligoribonucleotides using 2'-O-silylated ribonucleoside 3'-O-phosphoramidites on a controlled-pore glass support: synthesis of a 43-nucleotide sequence similar to the 3'-half molecule of an *Escherichia coli* formylmethionine tRNA," *J. Am. Chem. Soc.* 109:7845–7854 (1987).

Varga et al., "Infectious Entry Pathway of Adenovirus Type 2" *J. Virology* 65:6061–6070 (1991).

Verma, "Retroviral vectors for gene transfer" in *Microbiology–1985*, (Leive, et al., eds.), pp. 229–232, American Society for Microbiology:Washington, (1985).

Wang & Huang, "Highly efficient DNA delivery mediated by pH–sensitive immunoliposomes," *Biochemistry* 28(24):9508–14 (1989).

Wickham et al., "Integrins $\alpha_v\beta_3$ and $\alpha_v\beta_5$ Promote Adenovirus Internalization but Not Virus Attachment" *Cell* 73:309–319 (1993).

Wincott, et al., "Synthesis, deprotection, analysis and purification of RNA and ribozymes," *Nucleic Acids Res.* 23:2677–2684 (1995).

Wolff, et al., "Direct gene transfer into mouse muscle in vivo," *Science* 247(4949 Pt 1):1465–8 (1990).

Yaneva, et al., "Antibodies against Ku protein in sera from patients with autoimmune diseases," *Clin Exp Immunol* 76(3):366–72 (1989).

Yaneva, et al., "Expression of the Ku protein during cell proliferation," *Biochim Biophys Acta* 1090(2):181–7 (1991).

Yoo, et al., "Characterization of the RNA binding properties of Ku protein," *Biochemistry* 37:1336–43 (1998).

Zabner, "Adenovirus–Mediated Gene Transfer Transiently Corrects the Chloride Transport Defect in Nasal Epithelia of Patients with Cystic Fibrosis" *Cell* 75:207–216 (1993).

Zabner, "Safety and efficacy of repetitive adenovirus–mediated transfer of CFTR cDNA to airway epithelia of primates and cotton rats" *Nature Genetics* 6:75–83 (1994).

Zhang & Yaneva, "On the mechanisms of Ku protein binding to DNA," *Biochem Biophys Res Commun* 186(1):574–9 (1992).

Zhang, "Generation and identification of recombinant adenovirus by liposome–mediated transfection and PCR analysis" *Bio Techniques* 15:868–872 (1993).

Zhu, et al., "Systemic gene expression after intravenous DNA delivery into adult mice," *Science* 261(5118):209–11 (1993.

* cited by examiner

FIG. 4

OLIGOMERS THAT BIND TO KU PROTEIN

CROSS-REFERENCE TO RELATED APPLICATIONS

This application claims benefit of U.S. provisional application No. 60/070,278, filed Dec. 31, 1997.

STATEMENT REGARDING FEDERALLY FUNDED RESEARCH

The U.S. Federal Government has certain rights in this invention by virtue of grant number GM 35866 to William S. Dynan from the U.S. Public Health Service.

FIELD OF THE INVENTION

The present invention is generally in the area of oligomers, and more specifically in the area of nucleotide sequences that block the function of DNA-dependent protein kinase.

BACKGROUND OF THE INVENTION

Ku protein, a heterodimer of 70 kDa and 83 kDa polypeptides, is the regulatory component of the DNA-dependent protein kinase (DNA-PK). Ku protein binds to DNA discontinuities and is essential for DNA double-strand break repair.

Ku protein was first identified as an autoantigen in sera from certain patients with autoimmune disease (Mimori et al., J. Biol. Chem. 261, 2274–2278 (1986)). Subsequent characterization showed that Ku protein binds avidly to double-stranded DNA ends and other structural discontinuities in DNA such as nicks, gaps, and hairpins (Mimori & Hardin, J. Biol. Chem. 261, 10375–10379 (1986); Paillard & Strauss, Nucleic Acids Res. 19, 5619–5624 (1991); Zhang & Yaneva, Biochem. Biophys. Res. Commun. 186, 574–479 (1992); Blier et al., J. Biol. Chem. 268, 7594–7601 (1993); Falzon et al., J. Biol. Chem. 268, 10546–10552 (1993)). Further biochemical analysis demonstrated that Ku protein is the regulatory component of the DNA-dependent protein kinase (Dvir et al., Proc. Natl. Acad. Sci. USA 89, 11920–11924 (1992); Gottlieb & Jackson, Cell 72, 131–142 (1993)). In the presence of DNA ends, Ku protein can interact with the catalytic subunit of DNA-PK (DNA-PKcs) which is thereby targeted to the DNA. The ability of Ku protein to interact with DNA ends suggested that Ku and DNA-PKcs may play a role in DNA repair and recombination (Anderson, Trends Biochem. Sci. 18, 433–437 (1993)). Subsequent characterization of ionizing radiation-sensitive mutant cell lines showed that Ku protein and DNA-PKcs are essential for repair of DNA double-strand breaks and for V(D)J recombination (Getts & Stamato, J. Biol. Chem. 269, 15981–15984 (1994); Rathmell, Proc. Natl. Acad. Sci. USA 91, 7623–7627 (1994); Smider et al., Science 266, 288–291 (1994); Taccioli et al., Science 265, 1442–1445 (1994); Blunt et al., Cell 80, 813–823 (1995); Boubnov et al., Proc. Natl. Acad. Sci. USA 92, 890–894 (1995); Kirchgessner et al., Science 267, 1178–1183 (1995); Lees-Miller et al., Science 267, 1183–1185 (1995); Peterson et al., Proc. Natl. Acad. Sci. USA 92, 3171–3174 (1995)).

The binding of Ku protein to double-stranded DNA ends is largely sequence-independent. The ability of Ku protein to undergo facilitated transfer between DNA fragments with cohesive ends suggests that Ku protein may be able to interact transiently with two DNAs simultaneously, perhaps serving to align the ends for ligation (Bliss & Lane, J. Biol. Chem. 272, 5765–5773 (1997)). Consistent with this, recent atomic force microscopy and electron microscopy studies show images of Ku protein tethering DNA fragments together and participating in loop structures (Cary, Proc. Natl. Acad. Sci. USA 94, 4267–4272 (1997); Pang et al., Cancer Res. 57, 1412–1415 (1997)). There have also been a number of reports of possible sequence-specific binding of Ku protein to DNA (for example, Knuth et al., J. Biol. Chem. 265, 17911–17920 (1990); Messier et al., Proc. Natl. Acad. Sci. USA 90, 2685–2689 (1993); Okumura et al., FEBS Lett. 356, 94–100 (1994); Roberts et al., Proc. Natl. Acad. Sci., USA 91, 6354–6358 (1994)). Most recently, a sequence in the long terminal repeat of mouse mammary tumor virus has been characterized that appears to allow interaction of Ku protein with DNA in the absence of ends or single-stranded regions (Giffin et al., Nature 380, 265–268 (1996); Giffin et al., J. Biol. Chem. 272, 5647–5658 (1997)).

There is some evidence that Ku protein interacts with RNA, although this has been much less studied than the interaction with DNA. Antibodies to Ku protein stain both the nucleoplasm and the nucleolus. The amount of Ku protein in the nucleolus changes depending on the growth state of the cell, suggesting that this localization is actively regulated (Yaneva & Jhiang, Biochim. Biophys. Acta 1090, 181–187 (1991)). Separately, it has been demonstrated that nucleolar staining is sensitive to RNase treatment, whereas nucleoplasmic staining is not (Reeves, J. Exp. Med. 161, 18–39 (1985)). Thus, nucleolar localization may be regulated by interaction of Ku protein with RNA. Ku protein does not appear to bind to bulk tRNA or to synthetic RNA polymers (Mimori & Hardin, J. Biol. Chem. 261, 10375–10379 (1986)). However, one study showed that Ku protein forms a specific complex with an RNA that included the HIV trans-activation response (TAR) element sequence (Kaczmarski & Khan, Biochem. Biophys. Res. Commun. 196, 935–942 (1993)).

The Ku protein has been suggested to be involved in many important nuclear processes, including transcription, replication, and growth control, as well as DNA repair. It would be useful to have a means to demonstrate whether Ku protein is required for a biochemical activity (such as repair or recombination) that has been reconstituted in a crude cell-free system. It would also be useful to have a means to identify nuclear proteins that physically interact with Ku protein to exert their biological functions.

Ku protein and DNA-PK are important in the repair of radiation-induced DNA damage. If damage cannot be repaired, cells die. The cytotoxic effect of ionizing radiation forms the basis for radiation therapy, which is widely used in the treatment of human cancer. The efficacy of radiation therapy is currently limited by the radiation resistance of certain tumors (for example, glioblastomas) and by the side effects caused by irradiation of nearby normal tissues (for example, in treatment of breast and cervical cancer). Therefore, it would also be useful to have a means for sensitizing target cells and tissues to therapeutic radiation.

Some patients with autoimmune diseases such as systemic lupus erythematosus (SLE) and scleroderma produce anti-Ku antibodies. Ku is one of a number of proteins that are targets of autoantibodies in these patients. High levels of autoantibodies lead to deleterious consequences for the patient. It would be useful to have a compound directed against Ku protein to alter the course of autoimmune disease in patients with anti-Ku antibodies.

A problem in gene therapy is a loss of the foreign DNA from illegitimate recombination. It is believed that illegitimate recombination requires Ku-dependent double strand break repair. It would be useful to have a means to improve the stability of transgene DNA.

Therefore, it is an object of the disclosed invention to provide oligomers that bind to Ku protein.

It is also an object of the disclosed invention to provide oligomers that prevent illegitimate recombination to improve the stability of transgene DNA.

It is another object of the disclosed invention to provide oligomers that recognize Ku protein in a complex environment containing other macromolecules.

It is also an object of the disclosed invention to provide oligomers that improve the efficacy of radiation therapy by inhibiting DNA repair in the target cells.

It is also an object of the disclosed invention to provide oligomers to treat autoimmune disease in patients with anti-Ku antibodies.

It is also an object of the disclosed invention is to provide an assay for cellular proteins that interact with Ku protein or that promote or inhibit the interaction between Ku protein and DNA-PKcs.

It is also an object of the disclosed invention is to provide oligomers useful for manipulating the activity of Ku protein in cells and organisms to better understand its physiological role.

SUMMARY OF THE INVENTION

Disclosed are oligomers that bind Ku protein. These oligomers, also referred to herein as aptamers, are useful for inhibiting activation of DNA-PK, treating certain forms of autoimmune disease, detection and purification of Ku protein, and identification of proteins that interact with Ku protein. Preferably, the oligomers are composed of nucleotides, nucleotide analogs, or a combination. Most preferably, the oligomers are composed of ribonucleotides. Also disclosed is a method of inhibiting DNA repair, a method of identifying cellular proteins that interact with Ku protein, and a method of treating autoimmune disease in patients with anti-Ku antibodies.

The disclosed oligomers can have several preferred features, either alone or in combination, in addition to Ku binding. One such feature, referred to herein as inhibition activity, is inhibition of DNA-PK kinase activity. As discussed above, interaction of the Ku protein and DNA is involved in activation of DNA-PK kinase activity. Another preferred feature, referred to herein as aptamer motifs, is the presence of one or more of the base sequences GCUUUCCCANNNAC, (SEQ ID NO:20) A(A/C)AUGA, (SEQ ID NO:21) and AACUUCGA. These sequences—referred to herein as aptamer motif 1, aptamer motif 2, and aptamer motif 3, respectively—are associated with Ku binding capability. Another preferred feature, referred to herein as aptamer structure, is the presence of a structure similar to the structure shown in FIG. 6A. This structure has the general formula 5'-A-B-C-D-C'-E-A'-3', where A, B, C, D, C', E, and A' are components of the oligomer. In this structure, A and A' interact to form a stem structure, C and C' interact to form a stem structure, B and E make up a bulge region, and D is either a bulge or a loop. FIG. 6A depicts component D as a loop. Each of these preferred features (inhibition activity, aptamer motif, and aptamer structure) can be used either alone or in combination with one or both of the other characteristics.

BRIEF DESCRIPTION OF THE DRAWINGS

FIG. 4 is the predicted secondary structure of examples of the disclosed aptamers, SC4 ('5 to '3, SEQ ID NOs: 22, 6, and 23) and #2 ('5 to '3, SEQ ID NOs: 22, 5, and 23). RNA secondary structures were predicted using the methods of Zuker and co-workers (Jaeger et al., 1989; Jaeger et al., 1990) as implemented on the mfold World Wide Web server. Boldface indicates the conserved sequence motifs as shown in Table 1.

DETAILED DESCRIPTION OF THE INVENTION

Disclosed are oligomers that bind Ku protein. It is preferred that the oligomers bind Ku protein with a dissociation constant of less than 10 nM. These oligomers are useful for inhibiting activation of DNA-PK, treating certain forms of autoimmune disease, detection and purification of Ku protein, and identification of proteins that interact with Ku protein. Preferably, the oligomers are composed of nucleotides, nucleotide analogs, or a combination. Most preferably, the oligomers are composed of ribonucleotides. Also disclosed is a method of inhibiting DNA repair, a method of identifying cellular proteins that interact with Ku protein, and a method of treating autoimmune disease in patients with anti-Ku antibodies.

Figure 6A:
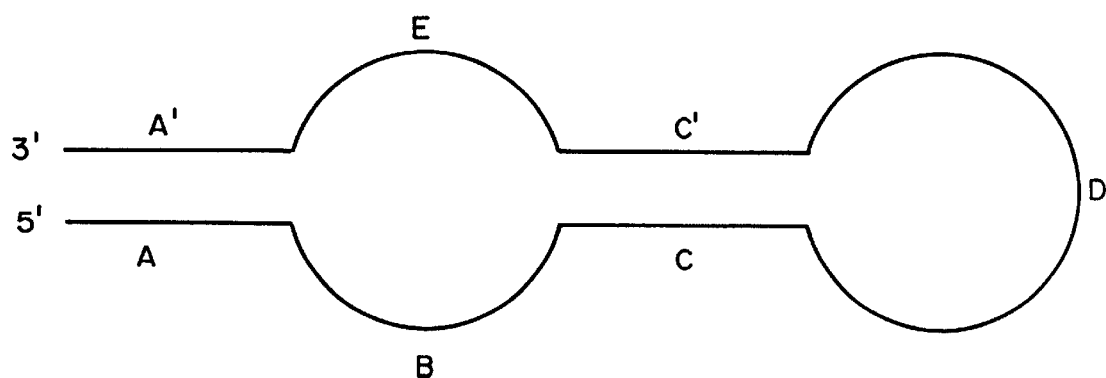
FIG. 6A is a representation of the general secondary structure for a preferred form of aptamer.
Figure 6B:
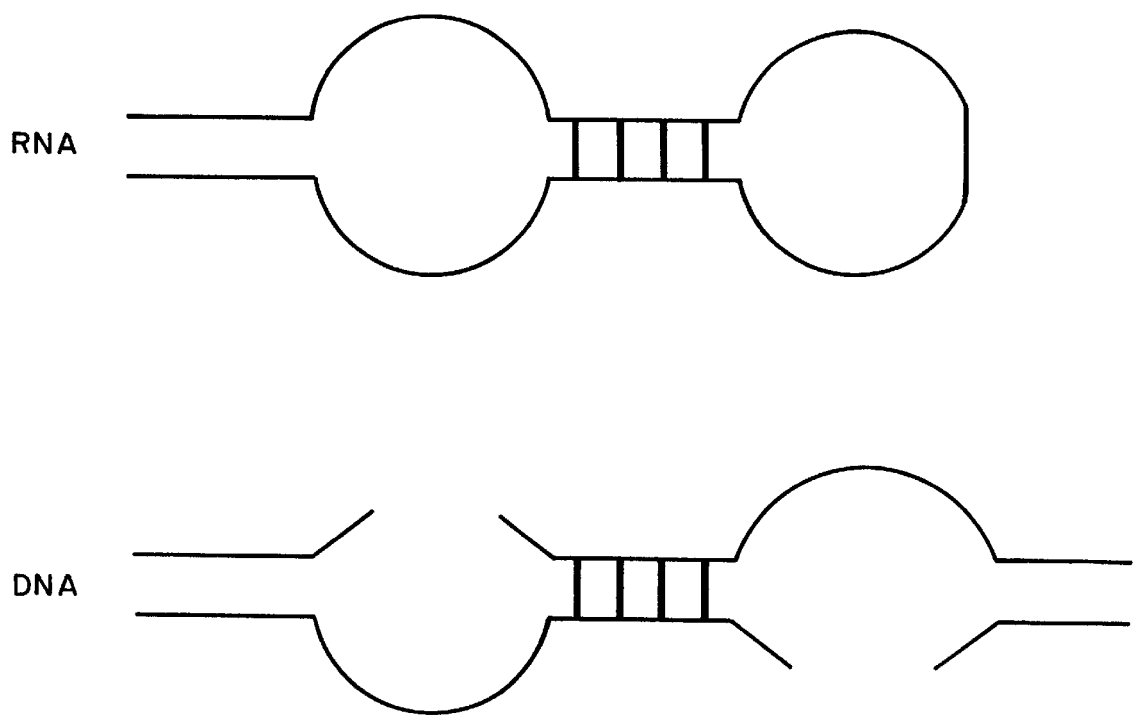
FIG. 6B is a comparison of the predicted secondary structure of a preferred form of aptamer with the secondary structure of a hypothetical double-strand DNA break repair intermediate.

The disclosed oligomers can have several preferred features, either alone or in combination, in addition to Ku binding. One such feature, referred to herein as inhibition activity, is inhibition of DNA-PK kinase activity. As discussed above, interaction of the Ku protein and DNA is involved in activation of DNA-PK kinase activity. Another preferred feature, referred to herein as aptamer motifs, is the presence of one or more of the base sequences GCUUUCCCANNNAC(SEQ ID NO:20), A(A/C)AUGA (SEQ ID NO:21), and AACUCGA. These sequences—referred to herein as aptamer motif 1, aptamer motif 2, and aptamer motif 3, respectively—are associated with Ku binding capability. Another preferred feature, referred to herein as aptamer structure, is the presence of a structure similar to the structure shown in FIG. 6A. This structure has the general formula 5'-A-B-C-D-C'-E-A'-3', where A, B, C, D, C', E, and A' are components of the oligomer. In this structure, A and A' interact to form a stem structure, C and C' interact to form a stem structure, B and E make up a bulge region, and D is either a bulge or a loop. FIG. 6A depicts component D as a loop. Each of these preferred features (inhibition activity, aptamer motif, and aptamer structure) can be used either alone or in combination with one or both of the other characteristics.

Examples of preferred oligomers are listed in Table 1. These oligoribonucleotides were identified as described in the examples. Only the portion of the selected oligomers that arose from the variable region of the pool RNA is shown in Table 1. That is, each of the oligonucleotides listed in Table 1 include the sequence GGGAGGAUAUUUUCUCAGACCGUAA(SEQ ID NO:22) at the 5' end and the sequence UUGCAGCAUCGUGAACUAGGAUC(SEQ ID NO:21) at the 3' end, although these sequences are not shown in Table 1. Thus, oligomer SC6 has the sequence GGGAGGAUAU-UUUCUCAGA CCGUAAGACUCACGAUGGAC-CAUACGCCUUCCCACUGGUCUUGUUA UUGCAGCAUCGUGAACUAGGAUC, (sequence represented by combined sequences of SEQ ID NOs: 22, 1, and 23, respectively) although only the sequence GACUCAC-GAUGGACCAUACGCCUUCC CACUGGUCUUGUUA (SEQ ID NO:1) is shown in the table.

Table 1 also discloses the dissociation constants (Kd) of the individual aptamers and the ability of the individual aptamers to inhibit DNA-PK activity. In a standard reaction, aptamers with a DNA-PK activity denoted as A had more than 85% inhibition, aptamers denoted as B had between 30 and 80% inhibition, and aptamers denoted with a C had under 30% inhibition.

TABLE 1

RNA Sequences and Kd values from the SELEX Procedure

| Name Frequency | Aligned sequence | DNA-PK Inhibition | $K_d$ |
|---|---|---|---|
| CLASS I | | | |
| SC6 (3) | GACUCACGAUGGACCAUAC<u>GCCUUCCCA</u>CUGGUCUUGUUA (SEQ ID NO:1) | C | 2.0 nM |
| #1-2 (1) | CAACACCUU<u>GCUUUCCCA</u>AUAC<u>CC</u>UGAAAUACAGUCGGAU (SEQ ID NO:2) | A | 1.5 nM |
| #1-17 (1) | UCCUUAUUUUAUG<u>GCUUUCCCA</u>CG<u>CAC</u>ACAAGCGUCUGCG (SEQ ID NO:3) | B | 3.2 nM |
| #85 (1) HYBRID | CAAGUAUCACGC<u>ACUUUCCCA</u>UUC<u>AC</u>UGUUAGAGACUGA (SEQ ID NO:4) | B | 0.7 nM |
| #2 (1) | GCCUAUGCACGG<u>AGCUUUCCCA</u>GCU<u>ACAGAUGA</u>AACCAGC (SEQ ID NO:5) | A | 0.3 nM |
| SC4 (8) | CCUAGUCUAAUCGAG<u>GCUUUCCCA</u>GUG<u>ACAAUGA</u>CCCAC (SEQ ID NO:6) | A | 1.7 nM |
| SC5 (4) | CUUGA<u>ACAUGA</u>UAGG<u>CUUACCCA</u>UAG<u>AC</u>AGAUUGACCCUU (SEQ ID NO:7) | A | 2.0 nM |
| CLASS II | | | |
| SC9 (3) | UGCCUUUAGCUGCG<u>ACAAUGA</u>ACAGCAUGACCUCACUAC (SEQ ID NO:8) | B | 0.6 nM |
| SC8 (8) | GUCCUUC<u>ACUAAUG</u>CUUACCAGACACACUAAGAACGUCAC (SEQ ID NO:9) | A | 0.6 nM |
| SC3 (3) | CAUUACCACAGUUCUAGCAUCCCGC<u>AAUG</u>GUAAGUCCGCA (SEQ ID NO:10) | B | 0.8 nM |
| SCI (23) | UUGUUCAACCUUGUCUAA<u>CAUGA</u>UACCGAUACGGACUACA (SEQ ID NO:11) | B | 1.2 nM |
| #84 (1) | AUCCGCGUACCGGGCUCA<u>AAUG</u>UCACUAUAGUAGAAAGCA (SEQ ID NO:12) | B | 1.8 nM |
| #52 (1) HYBRID | CUGAUCGUUC<u>AAUGA</u>CUAUUCUUUACCUUGAGUAACCGA (SEQ ID NO:13) | C | 3.2 nM |
| SC12 (4) | CUCGC<u>AACAUGACUUCGA</u>AAGUUUAAUCGUUCUUGUCAA (SEQ ID NO:14) | B | 0.5 nM |
| CLASS III | | | |
| #7-3 (1) | AGGUCGGCAUACAGAGUUCCGAAUGCGCG<u>UAACUUCGAC</u>U (SEQ ID NO:15) | A | 1.8 nM |
| SC11 (2) | CU<u>UAGUUUCGA</u>UCGAAGCUCAUUGGCCCAGCGUGGAUAAC (SEQ ID NO:16) | B | >10 nM |
| SC2 (12) | CACGCUCUACAACAGAUUGCGAAU<u>UAACUU</u>ACG<u>C</u>UUCAUA (SEQ ID NO:17) | A | 0.8 nM |
| #42 (1) OTHER | CAUCCUGGUAC<u>UCACUUCGAC</u>AUCGUACGUUCAAUCAUAC (SEQ. B) NO:18) | B | 4.5 nM |
| SC13 (3) | ACCUUUUUAGACGAACCUCAAAGUACAUUUAGUUGAAAAC (SEQ ID NO:19) | B | 0.8 nM |

RNA sequences are aligned to show maximum sequence identity. The underlined sequence indicates sequence identity within class.

Binding conditions were 25 mM Tris-HCl, pH 7.9, 0.5 mM EDTA, 10% glycerol, 5 mM MgCl$_2$, 0.5 mM DTT, and 0.01% Tween 20, and 120 mM KCl, at room temperature.

A. Oligomers

Figure 4:
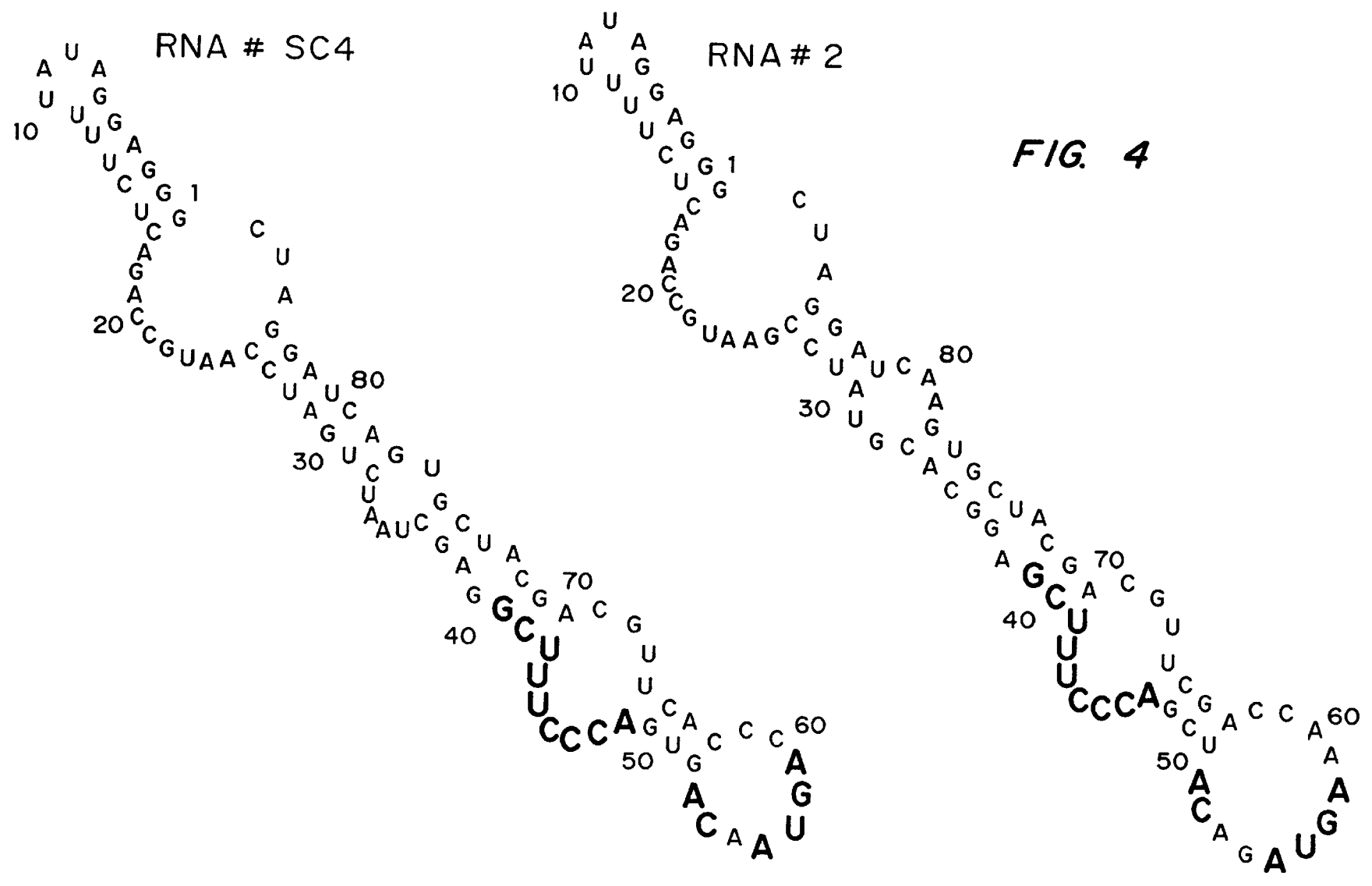

Some embodiments of the oligomers can be described generally by an oligonucleotide comprising the components A, B, C, D, C', E, and A'. Component A is the 5' most component and component A' is the 3' most component of the Ku binding oligonucleotides. Components A and A' interact in such a way as to form a stem structure through nucleotide base pairing. It is not required that all of the base pairs be contiguous, but it is recognized that those of skill in the art understand that the stability of any given double stranded nucleic acid molecule is a function of both the number of base pairs present and the number of bulges or mismatches that are present. A preferred embodiment has a stem that has a level of stability equivalent to two C:G base pairs. Another preferred embodiment has a purine:purine base pair, three base pairs from the bulge region comprised by components B and E (see FIG. 4).

Component B represents a bulge structure contiguous and 3' to component A. Furthermore, this component is preferably composed of pyrimidines. Most preferably this component contains the sequence 5'-UUUCCC-3' or 5'-UUUCCCA-3'.

Component C is contiguous and 3' to component B. Components C and C' form a stem region between the bulge formed by components B and E and the loop region D. It is also understood that this region can contain mismatches and bulges but that a certain level of stability is required. In preferred embodiments this stem will possess a stability equivalent to a stem made up of an AGCU:UCGA stem.

Component D is contiguous and 3' to component C. Component C' is contiguous and 3'- to component D. Component D is a sequence which preferably forms a loop structure. In a preferred embodiment component D contains the sequence 5'-ACNNAUGA-3'. In another preferred embodiment component D contains the sequence 5'-ACNNAUGANNNN-3'(SEQ ID NO:24). In another preferred embodiment component D contains 5'-ACMAUGANNNN-3'(SEQ ID NO:25) (where M is A or C). In a most preferred embodiment Component D contains the sequence 5'-ACAGAUGAAACC-3'(SEQ ID NO:26). It is also recognized that this loop structure can also be represented by a bulge-stem structure. Those in the art will recognize how to turn the loop structure into a bulge-stem structure. This would be done for example if there were two oligomers that were used to form the preferred structure.

Component E is contiguous and 3' to component C'. Component E is a bulged region. In the most preferred embodiment component B contains the sequence 5'-UGC-3'.
1. Oligomers Containing Chemically Modified Nucleotides.

RNA is relatively labile and can be degraded by a number of ribonucleases. This degradation can be greatly reduced by the introduction of modifications and substitutions at the 2'-prime position of the ribonucleotide and by modifications and substitutions along the phosphate backbone of the RNA. In addition a variety of modifications can be made on the nucleobases themselves which both inhibit degradation and which can increase desired nucleotide interactions or decrease undesired nucleotide interactions. Once the sequence of an aptamer is known modifications or substitutions can be made by the synthetic procedures described below or by procedures known to those of skill in the art. Aptamers with these various modifications can then be tested for function using any suitable assay for the Ku function of interest, such as the Ku protein binding assay or the inhibition of DNA-PK activity assay.

The oligomers disclosed are made up of nucleotides and/or nucleotide analogs or a combination of both, or are oligonucleotide analogues. The disclosed oligomers described by the general structure above may contain nucleotide analogs at positions which do not effect the function of the oligomer to bind Ku protein. The oligomeric sequences specifically interact with Ku protein, preferably at the DNA binding site of Ku protein.

Components A, A', B, C, C', D, and E are made up of nucleotides and nucleotide analogues in which the nucleotide and nucleotide analogs have the structure

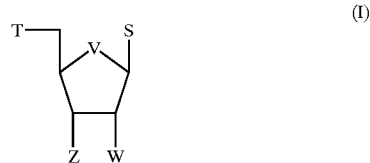

(I)

In structure (I) each S can be adenin-9-yl, cytosin-1-yl, guanin-9-yl, uracil-1-yl, uracil-5-yl, hypoxanthin-9-yl, thymin-1-yl, 5-methylcytosin-1-yl, 2,6-diaminopurin-9-yl, purin-9-yl, 7-deazaadenin-9-yl, 7-deazaguanin-9-yl, 5-propynylcytosin-1-yl, 5-propynyluracil-1-yl, isoguanin-9-yl, 2-aminopurin-9-yl, 6-methyluracil-1-yl, 4-thiouracil-1-yl, 2-pyrimidone-1-yl, quinazoline-2,4-dione-1-yl, xanthin-9-yl, $N^2$-dimethylguanin-9-yl or a functional equivalent thereof;

Each V can be an O, S, NH, or $CH_2$ group.

Each W can be —H, —OH, —COOH, —$CONH_2$, —$CONHR^1$, —$CONR^1R^2$, —$NH_2$, —$NHR^1$, —$NR^1R^2$, —$NHCOR^1$, —SH, $SR^1$, —F, —$ONH_2$, —$ONHR^1$, —$ONR^1R^2$, —NHOH, —$NHOR^1$, —$NR^2OH$, —$NR^2OR^1$, substituted or unsubstituted $C_1$–$C_{10}$ straight chain or branched alkyl, substituted or unsubstituted $C_2$–$C_{10}$ straight chain or branched alkenyl, substituted or unsubstituted $C_2$–$C_{10}$ straight chain or branched alkynyl, substituted or unsubstituted $C_1$–$C_{10}$ straight chain or branched alkoxy, substituted or unsubstituted $C_2$–$C_{10}$ straight chain or branched alkenyloxy, and substituted or unsubstituted $C_2$–$C_{10}$ straight chain or branched alkynyloxy. The substituents for W groups are independently halogen, cyano, amino, carboxy, ester, ether, carboxamide, hydroxy, or mercapto. $R^1$ and $R^2$ can be substituted or unsubstituted alkyl, alkenyl, or alkynyl groups, where the substituents are independently halogen, cyano, amino, carboxy, ester, ether, carboxamide, hydroxy, or mercapto.

T and Z are residues which together form a phosphodiester or phosphorothioate diester bond between adjacent nucleosides or nucleoside analogues or together form an analogue of an internucleosidic bond.

The 3' end of the disclosed oligomers can be protected against degradation by exonucleases by, for example, using a nucleotide analogue that is modified at the 3' position of the ribose sugar (for example, by including a substituted or unsubstituted alkyl, alkoxy, alkenyl, alkenyloxy, alkynyl or alkynyloxy group as defined above). The disclosed oligomers can also be stabilized against degradation at the 3' end by exonucleases by including a 3'-3'-linked dinucleotide structure (Ortigao et al., Antisense Research and Development 2:129–146 (1992)) and/or two modified phospho bonds, such as two phosphorothioate bonds.

The disclosed oligomers can also be linked to a prosthetic group in order to improve their cellular uptake and/or to enable a specific cellular localization. Examples of such prosthetic groups are polyamino acids (for example, polylysine), lipids, hormones or peptides. These prosthetic groups are usually linked via the 3' or 5' end of the oligomer either directly or by means of suitable linkers (for example, linkers based on 6-aminohexanol or 6-mercaptohexanol). These linkers are commercially available and techniques suitable for linking prosthetic groups to the oligomer are known to a person skilled in the art. The oligomers can also be produced as fusion oligonucleotides as discussed below.

In preferred oligomers, the oligonucleotides are made from RNA. The examples of Ku aptamers obtained as described in the examples are in the form of RNA. These RNAs were selected from a pool of about $10^{14}$ different RNA sequences using the systematic evolution of ligands by exponential enrichment (SELEX) procedure. Most of the selected RNAs bind to Ku protein with an equilibrium dissociation constant ($K_d$) $\leq 2$ nM, comparable to the affinity of DNA fragments for Ku protein under similar conditions. Many of the RNAs inhibited DNA-PK activity up to 85% by competing with DNA for a common binding site in Ku protein. None of the several RNAs tested activated DNA-PK in the absence of DNA.

2. Isolating RNAs That Bind Ku Protein.

There are several techniques that can be adapted for refinement of the disclosed aptamers or the selection of additional aptamers. Preferred are the techniques described in the examples. Other techniques can also be used. These include techniques generally referred to as "in vitro genetics" (Szostak, *TIBS* 19:89, 1992).

Molecules that inhibit or activate Ku mediated DNA-PK function can be isolated by screening for molecules that inhibit function of DNA-PK without inhibiting the interaction of DNA-PK with Ku protein. For example, molecules that inhibit DNA binding to DNA-PK may inhibit DNA-PK function without inhibiting DNA-PK:Ku interaction.

The disclosed aptamers can also be refined through the use of computer modeling techniques. Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other. These applications can be adapted to define and display the secondary structure of RNA and DNA molecules.

The pool of nucleic acid molecules from which the disclosed aptamers were isolated included invariant sequences flanking a variable sequence of approximately forty nucleotides. The 5' invariant region contained 27 nucleotides and the 3' invariant region contained 25 nucleotides. The invariant regions were used for the amplification of the molecules that were enriched through the SELEX procedure described below. This pool was chosen because it had been shown to function well in SELEX protocols. (Chen and Gold, Biochemistry 33, 8746–8756 (1994)).

3. Synthesis of Oligomers.

The disclosed oligomers can be synthesized using any suitable method. Many synthesis methods are known. The following techniques are preferred for synthesis of for example, 2'-O-Allyl modified oligomers that contain residual purine ribonucleotides, and bearing a suitable 3'-terminus such as an inverted thymidine residue (Ortigao et al., Antisense Research and Development 2:129–146 (1992)) or two phosphorothioate linkages at the 3'-terminus to prevent eventual degradation by 3'-exonucleases, can be synthesized by solid phase β-cyanoethyl phosphoramidite chemistry (Sinha et al., *Nucleic Acids Res.* 12:4539–4557 (1984)) on any commercially available DNA/RNA synthesizer. A preferred method is the 2'-O-tert-butyldimethylsilyl (TBDMS) protection strategy for the ribonucleotides (Usman et al., *J. Am. Chem. Soc.* 109:7845–7854 (1987)), and all the required 3'-O-phosphoramidites are commercially available. In addition, the use of aminomethylpolystyrene is preferred as the support material due to its advantageous properties (McCollum and Andrus *Tetrahedron Letters* 32:4069–4072 (1991)). Fluorescein can be added to the 5'-end of a substrate RNA during the synthesis by using commercially available fluorescein phosphoramidites. In general, a desired oligomer can be synthesized using a standard RNA cycle. Upon completion of the assembly, all base labile protecting groups are removed by an 8 hour treatment at 55° C. with concentrated aqueous ammonia/ethanol (3:1 v/v) in a sealed vial. The ethanol suppresses premature removal of the 2'-O-TBDMS groups which would otherwise lead to appreciable strand cleavage at the resulting ribonucleotide positions under the basic conditions of the deprotection (Usman et al., *J. Am. Chem. Soc.* 109:7845–7854 (1987)). After lyophilization the TBDMS protected oligomer is treated with a mixture of triethylamine trihydrofluoride/triethylamine/N-methylpyrrolidinone for 2 hours at 60° C. to afford fast and efficient removal of the silyl protecting groups under neutral conditions (Wincott et al., *Nucleic Acids Res.* 23:2677–2684 (1995)). The fully deprotected oligomer can then be precipitated with butanol according to the procedure of Cathala and Brunel (*Nucleic Acids Res.* 18:201 (1990)). Purification can be performed either by denaturing polyacrylamide gel electrophoresis or by a combination of ion-exchange HPLC (Sproat et al., *Nucleosides and Nucleotides* 14:255–273 (1995)) and reversed phase HPLC. For use in cells, it is preferred that synthesized oligomers be converted to their sodium salts by precipitation with sodium perchlorate in acetone. Traces of residual salts are then preferably removed using small disposable gel filtration columns that are commercially available. As a final step it is preferred that the authenticity of the isolated oligomers is checked by matrix assisted laser desorption mass spectrometry (Pieles et al., *Nucleic Acids Res.* 21:3191–3196 (1993)) and by nucleoside base composition analysis. In addition, a functional cleavage test with the oligomer on the corresponding chemically synthesized short oligoribonucleotide substrate is also preferred.

The disclosed oligomers can also be produced through enzymatic methods, when the nucleotide subunits are available for enzymatic manipulation. For example, the RNA molecules can be made through in vitro RNA polymerase T7 reactions. They can also be made by strains of bacteria or cell lines expressing T7, and then subsequently isolated from these cells. As discussed below, the disclosed aptamers can also be expressed in cells directly using vectors and promoters.

B. Pharmaceutical Compositions

The disclosed oligomers can be used in pharmaceutical mixtures that contain one or several oligomers as the active substance, and, optionally, pharmaceutically acceptable auxiliary substances, additives and carriers. Such pharmaceutical oligomers are suitable for the production of an agent to specifically inhibit Ku DNA binding activity in cells or inhibit the activity of DNA-PK. The disclosed oligomers can also be used for Ku inhibition and DNA-PK inhibition in plants or animals. Thus, the disclosed oligomers are expected to be useful as drugs for humans and animals as well as a pesticide for plants. As used herein, microparticles include liposomes, virosomes, microspheres and microcapsules formed of synthetic and/or natural polymers. Methods for making microcapsules and microspheres are known to those skilled in the art and include solvent evaporation, solvent casting, spray drying and solvent extension. Examples of useful polymers which can be incorporated into various microparticles include polysaccharides, polyanhydrides, polyorthoesters, polyhydroxides and proteins and peptides.

Liposomes can be produced by standard methods such as those reported by Kim et al., *Biochim. Biophys. Acta*, 728:339–348 (1983); Liu et al., *Biochim. Biophys. Acta*, 1104:95–101 (1992); and Lee et al., *Biochim. Biophys. Acta*, 1103:185–197 (1992); Wang et al., *Biochem.*, 28:9508–9514 (1989)). Such methods have been used to deliver nucleic acid molecules to the nucleus and cytoplasm of cells of the MOLT-3 leukemia cell line (Thierry and Dritschilo, *Nucl. Acids Res.*, 20:5691–5698 (1992)). Alternatively, the disclosed oligomers can be incorporated within microparticles, or bound to the outside of the microparticles, either ionically or covalently.

Cationic liposomes or microcapsules are microparticles that are particularly useful for delivering negatively charged compounds such as the disclosed compounds, which can bind ionically to the positively charged outer surface of these liposomes. Various cationic liposomes have previously been shown to be very effective at delivering nucleic acids or nucleic acid-protein complexes to cells both in vitro and in vivo, as reported by Felgner et al., *Proc. Natl. Acad. Sci. USA*, 84:7413–7417 (1987); Felgner, *Advanced Drug Delivery Reviews*, 5:163–187 (1990); Clarenc et al., *Anti-Cancer Drug Design*, 8:81–94 (1993). Cationic liposomes or microcapsules can be prepared using mixtures including one or more lipids containing a cationic side group in a sufficient quantity such that the liposomes or microcapsules formed from the mixture possess a net positive charge which will ionically bind negatively charged compounds. Examples of positively charged lipids that may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl]-N,N, N-triethylammonium ("DOTMA," see Felgner et al., *Proc. Natl. Acad. Sci USA*, 84:7413–7417 (1987); Felgner et al., *Nature*, 337:387–388 (1989); Felgner, *Advanced Drug Delivery Reviews*, 5:163–187 (1990)).

The disclosed oligomers can also be encapsulated by or coated on cationic liposomes which can be injected intravenously into a mammal. This system has been used to introduce DNA into the cells of multiple tissues of adult mice, including endothelium and bone marrow, where hematopoietic cells reside (see, for example, Zhu et al., *Science*, 261:209–211 (1993)).

C. Vectors And Expression Sequences

Delivery and expression of the disclosed oligomers can be facilitated by vectors and expression sequences. As used herein, plasmid or viral vectors are agents that transport the gene into the cell without degradation and include a promoter yielding expression of the gene in the cells into which it is delivered. In a preferred embodiment vectors are derived from either a virus or a retrovirus. Preferred viral vectors are Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Preferred retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors have higher transaction (ability to introduce genes) abilities than do most chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

1. Retroviral Vectors.

A retrovirus is an animal virus belonging to the virus family of Retroviridae, including any types, subfamilies, genus, or tropisms. Retroviral vectors, in general, are described by Verma, I. M., Retroviral vectors for gene transfer. In *MICROBIOLOGY*—1985, American Society for Microbiology, pp. 229–232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (*Science* 260:926–932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

2. Adenoviral Vectors.

The construction of replication-defective adenoviruses has been described (Berkner et al., *J. Virology* 61:1213–1220 (1987); Massie et al., *Mol. Cell. Biol.* 6:2872–2883 (1986); Haj-Ahmad et al., *J. Virology* 57:267–274 (1986); Davidson et al., *J. Virology* 61:1226–1239 (1987); Zhang "Generation and identification of recombinant adenovirus by liposome-mediated transfection and PCR analysis" *Bio Techniques* 15:868–872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580–1586 (1993); Kirshenbaum, *J. Clin. Invest.* 92:381–387 (1993); Roessler, *J. Clin. Invest.* 92:1085–1092 (1993); Moullier, *Nature Genetics* 4:154–159 (1993); La Salle, *Science* 259:988–990 (1993); Gomez-Foix, *J. Biol. Chem.* 267:25129–25134 (1992); Rich, *Human Gene Therapy* 4:461–476 (1993); Zabner, *Nature Genetics* 6:75–83 (1994); Guzman, *Circulation Research* 73:1201–1207 (1993); Bout, *Human Gene Therapy* 5:3–10 (1994); Zabner, *Cell* 75:207–216 (1993); Caillaud, *Eur. J. Neuroscience* 5:1287–1291 (1993); and Ragot, *J. Gen. Virology* 74:501–507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462–477 (1970); Brown and Burlingham, *J. Virology* 12:386–396 (1973); Svensson and Persson, *J. Virology* 55:442–449 (1985); Seth, et al., *J. Virol.* 51:650–655 (1984); Seth, et al., *Mol. Cell. Biol.* 4:1528–1533 (1984); Varga et al., *J. Virology* 65:6061–6070 (1991); Wickham et al., *Cell* 73:309–319 (1993)).

A preferred viral vector is one based on an adenovirus which has had the E1 gene removed and these virons are generated in a cell line such as the human 293 cell line. In another preferred embodiment both the E1 and E3 genes are removed from the adenovirus genome.

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

3. Expression Sequences.

Expression of the disclosed aptamers in cells also requires sequences to direct expression. It is preferred that an RNA polymerase III (pol III) promoter be used for expression. Pol III promoters generate transcripts that can be engineered to remain in the nucleus of the cell where Ku protein acts. It is preferred that a complete pol III transcription unit be used, including a pot III promoter, capping signal, and termination sequence. Pol III promoters, and other pol III transcription signals, are present in tRNA genes, 5S RNA genes, small nuclear RNA genes, and small cytoplasmic RNA genes. Preferred pol III promoters for use in aptamer expression vectors are the human small nuclear U6 gene promoter and tRNA gene promoters. The use of U6 gene transcription signals to produce short RNA molecules in vivo is described by Noonberg et al., *Nucleic Acids Res.* 22:2830–2836 (1994), and the use of tRNA transcription signals is described by Thompson et al., *Nucleic Acids Res.*, 23:2259–2268 (1995).

Many pol III promoters are internal, that is, they are within the transcription unit. Thus, these pol III transcripts include promoter sequences. To be useful for expression of aptamer molecules, these promoter sequences should not interfere with the structure or function of the aptamer. The U6 gene promoter is not internal (Kunkel and Pederson, *Nucleic Acids Res*, 17:7371–7379 (1989); Kunkel et al., *Proc. Natl. Acad Sci.* USA 83:8575–8579 (1986); Reddy etal., *J. Biol. Chem.* 262:75–81 (1987)). Suitable pol III promoter systems useful for expression of aptamer molecules are described by Hall et al., *Cell* 29:3–5 (1982), Nielsen et al., *Nucleic Acids Res.* 21:3631–3636 (1993), Fowlkes and Shenk, *Cell* 22:405–413 (1980), Gupta and Reddy, *Nucleic Acids Res.* 19:2073–2075 (1991), Kickhoefer et al., *J. Biol. Chem.* 268:7868–7873 (1993), and Romero and Blackburn, *Cell* 67:343–353 (1991). The use of pol III promoters for expression of RNA molecules is also described in WO 95/23225 by Ribozyme Pharmaceuticals, Inc.

In many contexts, it is preferred that expression of the aptamers is regulated, and in particular that the aptamers are expressed in a tissue- or cell-specific manner. For example, where a particular tissue or cell type is th therapeutic focus, expression directed at that tissue or cell type is preferred. Many tissue- and cell-specific promoters are known and can be used for the expression of the disclosed aptamers. An example of this type of promoter would be the prostate specific antigen promoter, which is specifically activated in prostate cells and has been utilized for the targeting of anticancer therapeutics of prostate tumors.

RNA fusion constructs can be produced which aid in the correct and specific targeting of expressed RNA molecules. These types of RNA fusion constructs are discussed in detail in Good et al., "Expression of Small Therapeutic RNAs in Cell Nuclei", *Gene Therapy*, 4:45–54 (1997). Expression vectors based on human tRNA(met) and U6 snRNA promoters are useful for targeting RNA expression and to render the resulting RNA transcripts more resistant to degradation.

Other promoters useful for expressing the disclosed oligomers in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature*, 273: 113 (1978)). The immediate early promoter of the human cytomegalovirus is conveniently obtained as a HindIII E restriction fragment (Greenway, P. J. et al., *Gene* 18: 355–360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus. Preferred examples are the SV40 enhancer on the late side of the replication origin (bp 100–270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

Figure 1:
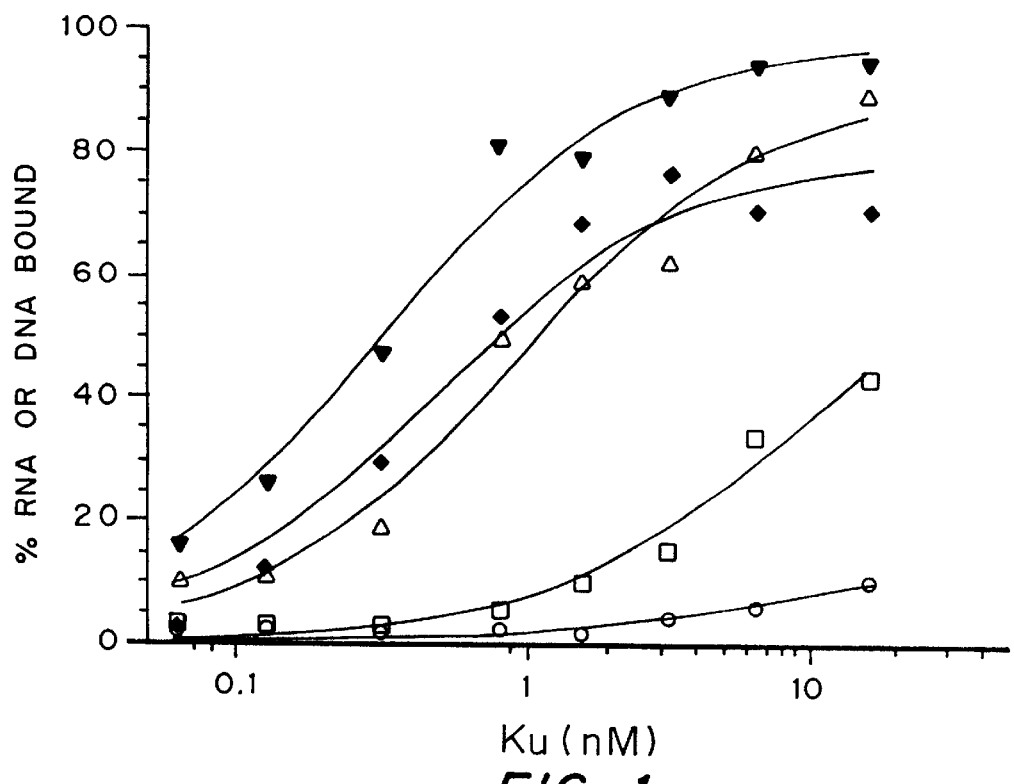
FIG. 1 is a graph of percent RNA or DNA bound versus concentration of Ku (nM) for five representative Ku protein-RNA and DNA binding curves obtained with an electrophoretic mobility shift assay. The graph shows that pooled RNA tested after the fourth and sixth round of Systematic Evolution of Ligands by Exponential Enrichment (SELEX; Tuerk & Gold, Science 249:505–510 (1990), and U.S. Pat. Nos. 5,270,163 and 5,567,588) had an increased ability to bind to Ku protein. Radiolabeled nucleic acid probes were as follows: □, nonselected RNA; ▽, RNA after 4th round of selection; ▲, RNA after 6th round of selection; O, HIV-TAR RNA (included for comparison); ♦, 21 base pair double-stranded DNA.

Expression vectors used in eukaryotic host cells (yeast, fungi, insect, plant, animal, human or nucleated cells) may also contain sequences necessary for the termination of transcription which may affect MRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In a preferred embodiment of the transcription unit, the polyadenylation region is derived from the SV40 early polyadenylation signal and consists of about 400 bases (FIG. 1). It is also preferred that the transcribed units contain other standard sequences alone or in combination with the above sequences improve expression from, or stability of, the construct.

D. Capture Tags

Isolation of Ku:oligomer complexes can be facilitated through the use of capture tags coupled to the oligomer. As used herein, a capture tag is any compound that can be associated with a synthesized RNA molecule and which can be used to separate compounds or complexes having the capture tag from those that do not. Preferably, a capture tag is a compound, such as a ligand or hapten, that binds to or interacts with another compound, such as a ligand-binding molecule or an antibody. It is also preferred that such interaction between the capture tag and the capturing component be a specific interaction, such as between a hapten and an antibody or a ligand and a ligand-binding molecule.

Suitable capture tags include hapten or ligand molecules that can be coupled to the 5' end of the synthesized RNA molecule. Preferred capture tags, described in the context of nucleic acid probes, have been described by Syvanen et al., *Nucleic Acids Res.*, 14:5037 (1986)). Preferred capture tags include biotin, which can be incorporated into nucleic acids (Langer et al., *Proc. Natl. Acad Sci. USA* 78:6633 (1981)) and captured using streptavadin or biotin-specific antibodies. A preferred hapten for use as a capture tag is digoxygenin (Kerkhof, *Anal. Biochem.* 205:359–364 (1992)). Many compounds for which a specific antibody is known or for which a specific antibody can be generated can be used as capture tags. Such capture tags can be captured by antibodies which recognize the compound. Antibodies useful as capture tags can be obtained commercially or produced using well established methods. For example, Johnstone and Thorpe, *Immunochemistry In Practice* (Blackwell Scientific Publications, Oxford, England, 1987), on pages 30–85, describe general methods useful for producingboth polyclonal and monoclonal antibodies.

Another preferred capture tag are anti-antibody antibodies. Such anti-antibody antibodies and their use are well known. For example, anti-antibody antibodies that are specific for antibodies of a certain class (for example, IgG, IgM), or antibodies of a certain species (for example, anti-rabbit antibodies) are commonly used to detect or bind other groups of antibodies. Thus, one can have an antibody to the capture tag and then this antibody:capture tag:RNA complex can then be purified by binding to an antibody for the antibody portion of the complex.

Another preferred capture tag is one which can form selectable cleavable covalent bonds with other molecules of choice. For example, a preferred capture tag of this type is one which contains a sulfer atom. An RNA molecule which is associated with this capture tag can be purified by retention on a thiolpropyl sepharose column. Extensive washing of the column removes unwanted molecules and reduction with β-mercaptoethanol, for example, allows the desired RNA molecules to be collected after purification under relatively gentle conditions (See Lorsch and Szostak, 1994 for a reduction to practice of this type of capture tag).

One preferred type of capture tag is a nucleotide cap analog, such as a 5'-5' guanosine dinucleotide cap. The capped aptamer would be incubated with a Ku-containing biochemical fraction, and a fusion protein containing the murine cap-binding protein would then be used to recover the aptamer-bound complex. This procedure has an advantage over antibody co-precipitation methods because the use of an aptamer that targets the DNA-binding site itself completely eliminates artifactual co-precipitation mediated by contaminating DNA, which is a major problem with co-precipitation of Ku protein. Bound proteins can be identified by SDS-PAGE, followed by other appropriate analytical methods.

Capture tags (and the associated oligomer) are isolated by interacting the capture tag with an appropriate molecule that binds the capture tag. These molecules, herein are referred to as capture tag receptors (CTRs). These CTRs can be associated with a solid support. When capture tag complexes are bound to CTRs attached to solid supports they can be effectively purified from the unwanted molecules because the solid support allows for successive washing to remove unbound molecules.

Supports that the CTRs can be coupled to can be any solid material to which the CTRs can be adhered or coupled. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Supports can have any useful form including thin films or membranes, beads, bottles, dishes, fibers, woven fibers, shaped polymers, particles and microparticles. Preferred forms of supports are plates and beads. The most preferred form of beads are magnetic beads.

Methods for immobilization of oligonucleotides to substrates are well established. Oligonucleotides, including oligonucleotide capture docks, can be coupled to substrates using established coupling methods. For example, suitable attachment methods are described by Pease et al., *Proc. Natl. Acad Sci. USA* 91(11):5022–5026 (1994), and Khrapko et al, *Mol Biol (Mosk) (USSR)* 25:718–730 (1991). A method for immobilization of 3'-amine oligonucleotides on casein-coated slides is described by Stimpson et al., *Proc. Natl. Acad Sci. USA* 92:6379–6383 (1995). A preferred method of attaching oligonucleotides to solid-state substrates is described by Guo et al., *NucleicAcids Res.* 22:5456–5465 (1994).

Methods for immobilizing antibodies to solid-state substrates are well established. Immobilization can be accomplished by attachment, for example, to animated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligand Techniques*, Craig T. Hermanson et al., eds. (Academic Press, New York, 1992). Antibodies can be attached to a support by chemically cross-linking a free amino group on the antibody to reactive side groups present within the solid-state support. For example, antibodies may be chemically cross-linked to a support that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

In addition, non-antibody proteins such as streptavidin, can be linked using similar methods. Many protein and antibody columns are commercially available as well as specifically derivatized supports for conjugation to the CTRs.

E. Kits

The disclosed oligomers can also be used in a reagent kit. For example, kits for identification of the Ku protein or proteins that bind the Ku protein which contains, for example, an oligomer and suitable buffer substances. In this case the oligomer and the buffer substances can be present in the form of solutions, suspensions or solids such as powders or lyophilisates. The reagents can be present together, separated from one another or optionally also on a suitable carrier. The disclosed oligomers can also be used as a diagnostic agent or to identify the function of unknown genes.

II. METHODS

The disclosed oligomers can be used for any purpose involving Ku binding to DNA, including methods to affect Ku activities and processes that depend on Ku activity and isolation of proteins that interact with Ku. For example, the disclosed oligomers can be used in pharmaceutical mixtures that contain one or several oligomers as the active substance, and, optionally, pharmaceutically acceptable auxiliary substances, additives and carriers. Such pharmaceutical oligomers are suitable for the production of an agent to specifically inhibit Ku DNA binding activity in cells or inhibit the activity of DNA-PK.

A. Method To Sensitize Cells To Agents

By introducing anti-Ku aptamers into cells, they can sensitize cells and tissues to the cytotoxic effects of therapeutic radiation and DNA-damaging drugs. This can be useful, for example, in cancer therapy where cancer cells can be made more sensitive to chemotherapeutic agents. Ku protein and DNA-PK are important in the repair of radiation-induced DNA damage. If damage cannot be repaired, cells die. The cytotoxic effect of ionizing radiation forms the basis for radiation therapy, which is widely used in the treatment of human cancer. The efficacy of radiation therapy is currently limited by the radiation resistance of certain tumors (for example, glioblastomas) and by the side effects caused by irradiation of nearby normal tissues (for example, in treatment of breast and cervical cancer). Therefore, it is expected to be useful to have a means for sensitizing target cells and tissues to therapeutic radiation.

Inhibition of Ku functions can leave cells more sensitive to a variety of agents such as agents that damage DNA (discussed above) and agents that interfere with DNA topoisomerase function. For example, etoposides prevent cell division by interfering with DNA topoisomerase function. Jin et al., "Differential Etoposide Sensitivity of Cells Deficient in the Ku and DNA-PKcs Components of the DNA-dependent Protein Kinase" *Carcinogenesis* 19:965–97 (1998), describe the increased sensitivity of cells with Ku mutations to etoposides, which are inhibitors of DNA Topoisomerase II. Thus, a preferred therapeutic use of the disclosed oligomers is in combination with agents that render cells more sensitive to reduced Ku function. In this context, the aptamers can increase the effectiveness of the agent.

B. Identification Of Cellular RNA Sequences Predicted That Bind Ku Protein

The disclosed aptamers are useful for identifying naturally occurring RNAs that bind to Ku protein. The existence of RNAs that bind tightly to Ku protein is consistent with suggestions that Ku protein function may be regulated to some extent by RNA in the normal cell. (Reeves, J. Exp. Med. 161, 18–39 (1985)). One site where such interactions might occur is in the nucleolus. The association of Ku protein with the nucleolus has been shown to be RNase sensitive (Reeves, J. Exp. Med. 161, 18–39 (1985)). A number of studies have shown that DNA-PK and Ku protein have an ability to regulate RNA polymerase I, which is localized in the nucleolus (Hoff et al., Proc. Natl. Acad. Sci. USA 91, 762–766 (1994); Kuhn et al., Genes and Development 9, 193–203 (1995); Labhart, Proc. Natl. Acad. Sci. USA 92, 2934–2938 (1995)). If, however, Ku protein associates with nucleolar RNAs, this would provide a potential targeting mechanism. Nucleoli contain a multitude of discrete small nucleolar RNAs, as well as nascent ribosomal RNA (reviewed in Smith & Steitz, Cell 89, 669–672 (1997)). The consensus sequences present in the aptamers can be used to predict whether particular nucleolar RNAs or other cellular RNAs are likely to bind to Ku protein. Cellular RNA sequences that become available in public databases can be searched to determine whether there is identity with the consensus sequences identified in the aptamers. Therefore, the disclosed aptamers are useful tools for predicting whether naturally occurring RNAs are likely to bind to Ku protein.

C. Identification Of Proteins That Interact With Ku Protein

The disclosed aptamers can also be used to identify proteins that interact with Ku protein. This can be accomplished, for example, by attaching a chemical capture tag to the aptamer which allows the aptamer to be captured on a solid matrix. Ku aptamers attached to a chemical capture tag can be isolated on, for example, a solid support. The aptamer can then be used to isolate Ku protein from a mixture. Any other molecules or proteins attached to the Ku protein can then be isolated also.

Another method to detect proteins that interact with Ku protein is to form complexes between radiolabeled aptamer and Ku protein, further incubate these complexes with the protein or mixture to be tested, and analyze the complexes by native polyacrylamide gel electrophoresis. The aptamer-Ku protein complexes migrate as a discrete species at a defined position. The mobility of this species will be shifted and it will be found at a different position on the gel when additional proteins are bound.

The same assay can be adapted to detect proteins that promote association of Ku protein and DNA-PKcs. Because the aptamers do not activate DNA-PK enzyme activity, it is expected that they will not, in themselves, promote assembly of Ku protein and DNA-PKcs into a functional DNA-PK complex. That is, when purified DNA-PKcs are incubated with aptamer-Ku protein complexes, there should be no shift in mobility. This property can serve as an assay for proteins that promote association of Ku protein and DNA-PKcs. Complexes will be formed between radiolabeled aptamer and Ku protein, and will be further incubated with DNA-PKcs and the protein or mixture to be tested. Complexes will be analyzed by native polyacrylamide gel electrophoresis. The mobility of the aptamer-Ku protein complex will be shifted when DNA-PKcs and additional proteins are bound. The presence of DNA-PKcs in the complex will be ascertained by determining whether monoclonal antibodies against DNA-PKcs further shift the mobility.

Although a number of antibodies to Ku protein have been described, aptamers have different and complementary properties. A variety of commercially available monoclonal antibodies (N3H10, N9C1, 111, 162, and S5C11) have been screened, as described in the examples, and all were found to produce supershifts in an electrophoretic mobility shift assay, indicating that they recognize epitopes outside the DNA binding site. By contrast, the aptamers competitively inhibited DNA binding, indicating that they are targeted directly to the DNA binding site of Ku protein. This property makes the aptamers uniquely useful for probing the role of Ku protein in various physiological processes.

D. Manipulation Of Ku Activity In Cells

The disclosed aptamers are also useful as tools for manipulation of Ku activity in cells. For this purpose, the aptamers should be expressed in or delivered to cells. There are a number of techniques that can be used for targeted expression of small RNAs in the nuclear compartment (Sullenger et al., Mol. Cell. Biol. 10, 6512–6523 (1990); Thompson et al., Nucleic Acids Res. 23, 2259–2268 (1995); Good et al., Gene Therapy 4:45–54 (1997)). Introduction of aptamers to cells will be useful for investigations of the physiological role of DNA-PK and other molecules and processes that Ku affects. Although DNA-PK is clearly involved in DNA repair, it has also been proposed that it is involved in a number of other processes, including the stress response, viral infection, and transcriptional regulation (McConnell & Dynan, Curr. Opin. Cell Biol. 8, 325–330 (1996) and references therein). A mechanism for manipulating DNA-PK activity in vivo is expected to provide a path for investigating the role of Ku protein in various physiological processes.

E. Use Of Aptamers To Treat Autoimmune Disease

The disclosed aptamers can also be used to treat autoimmune disease in patients producing anti-Ku antibodies. Antibodies to Ku protein occur in 15–20% of patients with systemic lupus erythematosus, scleroderma, myositis, and Sjogren's syndrome (Yaneva & Arentt, Clinical & Experimental Immunology 76, 366–372 (1989)). The immunogen in such cases may be a Ku protein-DNA complex, such as might be released from damaged or dying tissue. The disclosed aptamers can be used to disrupt such complexes, thus mitigating this chronic stimulus to the immune system.

For example, an aptamer may bind to Ku protein in a manner that does not allow an antibody to bind to Ku protein or may inhibit Ku protein binding to surface immunoglobulins on B cells. It has been suggested that self antigens are captured by antigen-specific receptors (surface immunoglobulins) on autoreactive B lymphocytes. (Craft and Fatenejad, *Arthritis and Rheumatism*, 40:1374–1382 (1997)). Thus, an aptamer that interferes with the binding of the Ku protein to the B cell, or which alters subsequent processing, is expected to block the chain of events leading to autoimmune disease.

F. Delivery Of Oligomers To Cells

A variety of methods are available for delivering the disclosed oligomers to cells. For example, in general, the disclosed oligomers can be incorporated within or on microparticles or liposomes. Microparticles or liposomes containing the disclosed oligomers can be administered systemically, for example, by intravenous or intraperitoneal administration, in an amount effective for delivery of the disclosed oligomers to targeted cells. Other possible routes include trans-dermal or oral, when used in conjunction with appropriate microparticles. Generally, the total amount of the liposome-associated oligomer administered to an individual will be less than the amount of the unassociated oligomer that must be administered for the same desired or intended effect.

Oligomers including various polymers such as the polylactic acid and polyglycolic acid copolymers, polyethylene, and polyorthoesters and the disclosed oligomers can be delivered locally to the appropriate cells by using a catheter or syringe. Other means of delivering such oligomers locally to cells include using infusion pumps (for example, from Alza Corporation, Palo Alto, Calif.) or incorporating the oligomers into polymeric implants (see, for example, Johnson and Lloyd-Jones, eds., *Drug Delivery Systems* (Chichester, England: Ellis Horwood Ltd., 1987), which can effect a sustained release of the therapeutic oligomers to the immediate area of the implant.

Delivery of the disclosed oligomers can be facilitated by targeting them to particular tissue or cell types. For example, the disclosed oligomers may be targeted to a particular cell type via antibodies, receptors, or receptor ligands. The following references are examples of the use of this technology to target specific proteins to tumor tissue (Senter, et al., *Bioconjugate Chem.*, 2:447–451, (1991); Bagshawe, K. D., *Br. J. Cancer*, 60:275–281, (1989); Bagshawe, et al., *Br. J. Cancer*, 58:700–703, (1988); Senter, et al., *Bioconjugate Chem.*, 4:3–9, (1993); Battelli, et al., *Cancer Immunol. Immunother.*, 35:421–425, (1992); Pietersz and McKenzie, *Immunolog. Reviews*, 129:57–80, (1992); and Roffler, et al., *Biochem. Pharmacol*, 42:2062–2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214–6220, (1989); and Litzinger and Huang, *Biochimica et Biophysica Acta*, 1104:179–187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399–409 (1991)).

The oligomers can also be delivered to cells and expressed within the targeted cells using gene transfer technology based on viral and retroviral vectors. Gene transfer can be obtained using direct transfer of genetic material, in a plasmid or viral vector, or via transfer of genetic material. Further, these methods can be used to target certain diseases and cell populations by using the targeting characteristics of the carrier. Transfer vectors can be any nucleotide construction used to deliver genes into cells (e.g., a plasmid), or as part of a general strategy to deliver genes, e.g., as part of recombinant retrovirus or adenovirus (Ram et al. *Cancer Res.* 53:83–88, (1993)). Appropriate means for transfection, including viral vectors, chemical transfectants, or physico-mechanical methods such as electroporation and direct diffusion of DNA, are described by, for example, Wolff, J. A., et al., *Science*, 247, 1465–1468, (1990); and Acsadi et al., *Nature*, 352, 815–818, (1991).

III. DEFINITIONS

As used herein, the term "aptamer" is an oligomer or oligonucleotide that folds into a specific conformation and binds a target biomolecule.

As used herein, oligomer refers to oligomeric molecules composed of subunits where the subunits can be of the same class (such as nucleotides) or a mixture of classes (such as nucleotides and ethylene glycol). It is preferred that the disclosed oligomers be oligomeric sequences, non-nucleotide linkers, or a combination of oligomeric sequences and non-nucleotide linkers. It is more preferred that the disclosed oligomers be oligomeric sequences. Oligomeric sequences are oligomeric molecules where each of the subunits includes a nucleobase (that is, the base portion of a nucleotide or nucleotide analogue) which can interact with other oligomeric sequences in a base-specific manner. The hybridization of nucleic acid strands is a preferred example of such base-specific interactions. Oligomeric sequences preferably are comprised of nucleotides, nucleotide analogues, or both, or are oligonucleotide analogues.

Non-nucleotide linkers can be any molecule, which is not an oligomeric sequence, that can be covalently coupled to an oligomeric sequence. Preferred non-nucleotide linkers are oligomeric molecules formed of non-nucleotide subunits. Examples of such non-nucleotide linkers are described by Letsinger and Wu, (*J. Am. Chem. Soc.* 117:7323–7328 (1995)), Benseler et al., (*J. Am. Chem. Soc.* 115:8483–8484 (1993)) and Fu et al. , (*J. Am. Chem. Soc.* 116:4591–4598 (1994)). Preferred non-nucleotide linkers, or subunits for non-nucleotide linkers, include substituted or unsubstituted $C_1$–$C_{10}$ straight chain or branched alkyl, substituted or unsubstituted $C_2$–$C_{10}$ straight chain or branched alkenyl, substituted or unsubstituted $C_2$–$C_{10}$ straight chain or branched alkynyl, substituted or unsubstituted $C_1$–$C_{10}$ straight chain or branched alkoxy, substituted or unsubstituted $C_2$–$C_{10}$ straight chain or branched alkenyloxy, and substituted or unsubstituted $C_2$–$C_{10}$ straight chain or branched alkynyloxy. The substituents for these preferred non-nucleotide linkers (or subunits) can be halogen, cyano, amino, carboxy, ester, ether, carboxamide, hydroxy, or mercapto.

As used herein, nucleoside refers to adenosine, guanosine, cytidine, uridine, 2'-deoxyadenosine, 2'-deoxyguanosine, 2'-deoxycytidine, or thymidine. A nucleoside analogue is a chemically modified form of nucleoside containing a chemical modification at any position on the base or sugar portion of the nucleoside. As used herein, the term nucleoside analogue encompasses, for example, both nucleoside analogues based on naturally occurring modified nucleosides, such as inosine and pseudouridine, and nucleoside analogues having other modifications, such as modifications to the 2' position of the sugar. As used herein, nucleotide refers to a phosphate derivative of nucleosides as described above, and a nucleotide analogue is a phosphate derivative of nucleoside analogues as described above. The subunits of oligonucleotide analogues, such as peptide nucleic acids, are also considered to be nucleotide analogues.

As used herein, a ribonucleotide is a nucleotide having a 2' hydroxyl function. Analogously, a 2'-deoxyribonucleotide is a nucleotide having only 2' hydrogens. Thus, ribonucleotides and deoxyribonucleotides as used herein refer to naturally occurring nucleotides having nucleoside components adenosine, guanosine, cytidine, and uridine, or 2'-deoxyadenosine, 2'-deoxyguanosine, 2'-deoxycytidine, and thymidine, respectively, without any chemical modification. Ribonucleosides, deoxyribonucleosides, ribonucleoside analogues and deoxyribonucleoside analogues are similarly defined except that they lack the phosphate group, or an analogue of the phosphate group, found in nucleotides and nucleotide analogues.

As used herein, oligonucleotide analogues are polymers of nucleic acid-like material with nucleic acid-like properties, such as sequence dependent hybridization, that contain at one or more positions, a modification away from a standard RNA or DNA nucleotide. A preferred example of an oligonucleotide analogue is peptide nucleic acid.

As used herein, base pair refers to a pair of nucleotides or nucleotide analogues which interact through one or more hydrogen bonds. The term base pair is not limited to interactions generally characterized as Watson-Crick base pairs, but includes non-canonical or sheared base pair interactions (Topal and Fresco, *Nature* 263:285 (1976); Lomant and Fresco, *Prog. Nucl. Acid Res. Mol. Biol.* 15:185 (1975)).

As used herein the term "gene" when used in the context of genetic vectors refers to the genetic material of interest that is to be transferred to the host organism. For example, the "gene" to be transferred could be a sequence which codes for an aptamer and when transcribed would produce a finctional aptamer.

The present invention will be further understood by reference to the following examples.

EXAMPLES

Example 1

Preparing the RNA Pool and Screening for Ku Protein Binding

Because there was little previous information about Ku protein-RNA interactions, the RNA binding properties of Ku protein were systematically investigated using SELEX (systematic evolution of ligands by exponential enrichment) technology. With this technology, it is possible to identify oligonucleotides from a large, random pool that bind to a ligand of interest. The SELEX method has been used to identify oligonucleotides that bind to nucleic acid binding proteins, to non-nucleic acid binding proteins, and to small molecules (reviewed in Gold et al., *Annu. Rev. Biochem.* 64, 763–797 (1995)).

The RNA pool was prepared by synthesis of single stranded RNA from a template comprising a region of conserved sequences and a region of randomized and/or biased sequences.

Synthesis of the RNA Pool

SELEX protocols and the template used to synthesize the nonselected RNA pool were obtained from Dr. Hang Chen and Dr. Larry Gold (University of Colorado) and modified as described below. The major change to the SELEX protocol was to increase the KCl concentration during sequential rounds of SELEX to maintain stringency. Protocols can also be obtained from Tuerk & Gold, *Science* 249, 505–510 (1990), and U.S. Pat. Nos. 5,270,163 and 5,567,588, incorporated herein by reference. HeLa cell nuclear extracts and oligonucleotides were obtained from Dr. Mark Anderson and Ms. Kirsten Strickler. Chemicals were obtained from Sigma, Fisher Scientific, antibodies from Neomarkers, nitrocellulose filters from Millipore, cloning vectors from Promega and Invitrogen, translation kits from Ambion, and RNasin from Promega.

SELEX procedures to select Ku binding RNAs were carried out largely as described in Chen & Gold, Biochemistry 33, 8746–8756 (1994). The template for synthesis of the starting RNA pool was based on a DNA oligonucleotide, 5'-CCCGGATCCTAGTTCACGATGCTGCAA-$(N)_{40}$-TTACGGTCTGAGAAAATATCCTCCC-3'(SEQ ID NO:27), where N indicates an equimolar mixture of A, G, C and T. This sequence was used because it is known to function well in SELEX. The 5' and 3' constant regions do not bind to Ku protein. DNA templates were generated by PCR amplification of this oligonucleotide using primer 1, 5'-CCCAAGCTTAATAC GACTCACTATAGGGAG-GATATTTTC TCAGACCGTAA-3'(SEQ ID NO:28), and primer 2, 5'-CCCGGATCCTAGTTCACGATGC TGCAA-3'(SEQ ID NO:29). Amplification was carried out with 0.5 μM of the oligonucleotide containing the random segment, 2 μM primer 1 and primer 2, 1 mM dATP, dCTP, dGTP, and dTTP, 50 U/ml Taq DNA polymerase, 50 mM KCl, 10 mM Tris-HCl, pH 8.4, 7.5 mM $MgCl_2$, and 50 μg/mL BSA in a volume of 0.5 ml. After four cycles of amplification (93° C. for 30 s, 57° C. for 20 s, 73° C. for 90 s), the reaction was extracted with an equal volume of phenol-chloroforn-isoamyl alcohol (25:24:1 v/v/v) (PCIA), and nucleic acids were precipitated from the supernatant by addition of 0.1 vol of 3 M NaOAc pH 5.2 and 2.5 vol ethanol.

This template preparation was incubated for 2–3 h at 37° C. in a reaction mixture containing 475 U/ml T7 RNA polymerase, 40 mM Tris-HCl, pH 8.0, 12 mM $MgCl_2$, 5 mM DTT, 1 mM spermidine, 0.002% Triton X-100, 4% PEG 8000, 2 mM ATP, UTP, and GTP, and 0.2 mM [a-$^{32}$P] CTP (1 Ci/mmol) in a final volume of 200 μl. DNase I was added (25 U/ml) and incubation was continued for 30 minute. The resulting RNAs were fractionated by 10% urea-PAGE and gel slices containing full-length 92 nucleotide RNA were excised, crushed, mixed with 0.5 ml TE, 0.5 ml phenol, and 10 μl 10% sodium dodecyl sulfate, and tumbled overnight at 4° C. to extract RNA. The supernatant was collected and RNA was precipitated with NaOAc and EtOH as described above. RNA was dissolved in TE, denatured at 100° C. for 2 minute, and renatured by adjusting to 5 mM $MgCl_2$, cooling rapidly to 0° C., and incubating for 30 minute. The amount of RNA recovered was estimated by liquid scintillation counting.

Protein Purification

Native DNA-PKcs and Ku protein were purified from HeLa cell nuclear extracts as previously described in Dvir et al., J. Biol. Chem 268(14):10440–10447 (1993), except that the Phenyl-Superose and Mono S steps were omitted. Monoclonal antibodies to Ku protein were obtained from Neomarkers (Fremont, Calif.).

Selection of Ku-binding RNAs

To perform in vitro selections, the RNA pool was mixed with purified Ku protein under conditions for complex binding. RNA and Ku protein were incubated for 30 minute at room temperature in a buffer containing 25 mM Tris-HCl, pH 7.9, 0.5 mM EDTA, 10% glycerol, 5 mM $MgCl_2$, 0.5 mM DTT, and 0.01% Tween 20 in a final volume of 50–100 μl. Concentrations of RNA, Ku protein, and KCl were variable, as specified in Table 2. Ku protein-RNA complexes were isolated by electrophoresis on a 5% non-denaturing polyacrylamide gel containing 25 mM Tris-HCl, pH 8.3, 190 mM glycine, and 1 mM EDTA at 300 V for one hour. In one experiment, complexes were isolated by passage over a nitrocellulose filter (Millipore 25-μm HAWP), which was washed twice with 5 ml of 25 mM Tris-HCl, pH 7.9. RNA was eluted from the polyacrylamide gel or the filter by tumbling in a mixture of TE, phenol, and SDS as described above.

The RNAs having a high affinity for the Ku protein relative to the mixture were partitioned by nitrocellulose filter binding and electrophoretic mobility shift assay. Another way to separate complexes is by immunoprecipitation.

Once the enriched RNA molecules were separated from the isolated complexes, they were amplified by reverse transcription followed by polymerase chain reaction. The complexity of a selected pool can be characterized by direct sequencing or restriction enzyme analysis.

Additional Rounds of SELEX Selection and Amplification

When additional rounds of selection were performed, purified Ku protein (from HeLa cell nuclear extracts) was mixed with the RNA pool and allowed to bind. Ku-RNA complexes were isolated using either a nitrocellulose filter binding or an electrophoretic mobility shift assay (EMSA). RNA that was bound to Ku protein was isolated, amplified by RT-PCR, and again enriched based on the ability to bind to Ku protein. The selected RNA was reverse-transcribed by incubating in a reaction mixture containing 50 mM Tris-HCl, pH 8.3, 60 mM NaCl, 6 mM Mg(OAc)2, 10 mM DTT, 0.4 mM dATP, dCTP, dGTP, and dTTP, and 300 U/ml of AMV reverse transcriptase, in a final volume of 50 μl. The resulting cDNA was amplified by 15 cycles of PCR using primers 1 and 2 at 93° C. for 30 seconds, 58° C. for 20 seconds, 72° C. for 90 seconds. This process was repeated 6–7 times. Selection conditions used for each round of selection are given in Table 2. To maintain the stringency of selection, the RNA:protein ratio, the KCl concentration, or both were progressively increased as shown in Table 2. Two independent selections were conducted using different batches of starting RNA.

After six or seven rounds of selection, cDNA was synthesized from the final RNA pool and amplified by 5 cycles of PCR using primer 1 and 2. The product was digested with Bam HI and Hind III and subcloned into the Bam HI and Hind III sites of pGEM3zf(+) (Promega) or pZero2.1 (Invitrogen). Inserts were sequenced with an m13 reverse primer using an ABI automated sequencer.

TABLE 2

Summary of the Selection Parameters

| SELEX Round | Input RNA (nM) | Ku protein[a] (nM) | KCl[b] (mM) | Selection[c] Method |
|---|---|---|---|---|
| Selection I | | | | |
| 1 | 1305 | 64.1 | 50 | NCFA |
| 2 | 612.5 | 24.3 | 50 | EMSA |
| 3 | 860 | 42.6 | 120 | EMSA |
| 4 | 1130 | 42 | 120 | EMSA |
| 5 | 2320 | 64 | 150 | EMSA |
| 6 | 142 | 3.2 | 160 | EMSA |
| Selection II | | | | |
| SELEX Round | Input RNA (nM) | Ku protein (nM) | KCl (mM) | Selection Method |
| 1 | 1330 | 53 | 120 | EMSA |
| 2 | 1660 | 42 | 120 | EMSA |
| 3 | 456 | 14.9 | 150 | EMSA |
| 4 | 144 | 3.84 | 160 | EMSA |
| 5 | 1065 | 21.3 | 160 | EMSA |
| 6 | 2710 | 18.6 | 160 | EMSA |
| 7 | 436 | 2.4 | 160 | EMSA |

[a]The ratio of Ku protein to input RNA was gradually decreased in order to increase the stringency.
[b]Salt concentration was increased to maintain high stringency.
[c]Nitrocellulose filter binding assay (NCFA) or electrophoretic mobility shift assay (EMSA) were employed for selection methods.

RNAs from the last round of selection were cloned and sequenced using standard techniques. Table 1 presents the sequence of nineteen aptamer RNAs that were isolated that bind avidly to Ku protein. Many of the RNAs contain common sequence motifs. A number of the RNAs bind competitively with DNA to Ku protein and thereby inhibit DNA and PK enzymatic activity. The ability of Ku protein to bind tightly to specific RNAs is consistent with a role for RNA in the regulation of Ku protein activity or intranuclear localization. Additionally, the identification of diverse RNAs that bind avidly to Ku protein raises the possibility that natural RNAs modulate the activity of DNA-PK in vivo.

Binding of Ku Protein

Binding of RNA and DNA to Ku protein was measured using EMSA as shown by the representative Ku protein-RNA binding curves after successive rounds of SELEX in FIG. 1. Binding curves were obtained with EMSA followed by a nonlinear least squares fit of the data. The RNA pools in FIG. 1 were transcribed from templates prior to the first round (nonselected), and after the fourth (4th), and the sixth (6th) rounds of SELEX using T7 RNA polymerase as described in example 2. A twenty-one base pair double-stranded DNA was end-labeled with T4 polynucleotide kinase. The DNA was arbitrarily chosen as a transcription factor binding site from the human T-cell leukemia virus proviral promoter, 5'-CTCAGGCGTTGACGACAACCC-3' (SEQ ID NO:30).

Ku protein bound to nonselected RNA with an apparent average $K_d$ of 24 nM. This binding was somewhat stronger than expected, given that previous work had found that Ku protein had little ability to interact with tRNA or synthetic RNA polymers (Mimori & Hardin, J. Biol. Chem. 261, 10375–10379 (1986)). Pooled RNA tested after the 4th and 6th round of SELEX showed an increased ability to bind to Ku protein. RNA obtained after the 6th round of selection bound with an apparent $K_d$ of about 0.3 nM, which was comparable to the binding seen with a double-stranded DNA oligonucleotide under similar conditions. Although the average affinity of the selected RNA was only 75-fold greater than for the nonselected pool, subsequent experiments revealed clear functional differences, as only the selected RNAs were able to inhibit biochemical activities of Ku protein.

Example 2

Comparison of Binding of RNAs to Determine Specificity

Synthesis of Aptamer RNAs

Individual aptamer RNAs were synthesized by T7 RNA polymerase using linearized plasmid template. Both radiolabeled RNA and nonradiolabeled RNA were prepared using a MEGA shortscript T7 kit (Ambion) with 8 μg linearized plasmid template. The RNA was gel-purified, heated, and refolded as described in example 1, and the final concentration was determined spectrophotometrically. Secondary structures were predicted using the method of Zuker (Jaeger et al., Proc. Natl. Acad. Sci. USA 86, 7706–7710 (1989); Jaeger et al., Meth. Enzymol. 183, 281–306 (1990)) as implemented on the mfold server www.ibc.wustl.edu/%7Ezuker/rna/form 1.cgi).

Synthesis of RNA Containing the TAR Sequence

Pools of RNA at various stages of selection were also characterized directly for their ability to bind to Ku protein in an electrophoretic mobility shift assay. For comparison of the aptamer RNAs binding affinity with other known RNAs, these assays also included a HIV TAR RNA, which was synthesized by T7 RNA polymerase as described in the preceding section. This RNA consisted of the following HIV-derived sequence: GGGUCUCUCUGGUUAGACCA-GAUCUGAGCCUGGGAGCUCUCUGGC UAACUAGGGAACCC(SEQ ID NO:31).

TAR-containing RNAs have previously been reported to bind selectively to Ku protein (Kaczmarski & Khan, Biochem. Biophys. Res. Commun. 196, 935–942 (1993)).

Binding of the TAR RNA was measurable, but weak, under the conditions of the experiments. These results confirm that TAR-containing RNA has some ability to bind to Ku protein, but indicate that the binding is not particularly strong, relative to other short RNAs. An in vitro yeast tRNA transcript also bound very weakly to Ku protein.

Example 3

Cloning, Sequence Analysis of Aptamers, and $K_d$ of Aptamers

After six and seven rounds of SELEX (Selection I and II in Table 2, respectively), the pooled RNA was reverse-transcribed, PCR-amplified, and cloned into plasmid vectors. 82 clones were isolated, including 63 from Selection I and 19 from Selection II. Allowing for duplicates, the 82 clones represented 19 independent sequences, which are given in Table 1.

An equilibrium dissociation constant was determined for the binding of each of the 19 different RNAs to Ku protein. The results, given in Table 1, showed that most of the RNAs have a $K_d$ of less than 2 nM.

The sequence alignment in Table 1 revealed that the RNAs can be grouped into three classes, based on the presence of conserved sequence motifs in the variable region of each aptamer. The most striking of these motifs was a sequence, GCUUUCCCANNNAC (herein designated SEQ ID NO:20) (wherein N may be A, C, G or T), which was perfectly conserved in three independent RNA sequences and partially conserved in four others. A second motif, AMAUGA (herein designated SEQ ID NO:21) (wherein M may be either A or C) was perfectly conserved in three RNAs and partially conserved in seven others. A third motif, which partially overlaps the second, had the sequence AACUUCGA (bases 31–38 of SEQ ID NO:15). This motif was present in one RNA and partially conserved in four others. Several RNAs fell into hybrid classes containing two of the three motifs. Subsequent analysis showed that the hybrid RNAs containing two motifs were among the most efficacious blockers of Ku protein activity in functional assays.

Example 4

Inhibition of DNA-PK Activity by Different RNA Aptamers

Binding of the RNA aptamers to Ku protein to determine if they are capable of regulating Ku protein activity was then measured. One of the major biochemical functions of Ku protein is to regulate the activity of DNA-PK. Ku protein targets the catalytic subunit of DNA-PK (DNA-PKcs) to DNA, increasing phosphorylation activity by 5–50 fold (Dvir et al., Proc. Natl. Acad. Sci. USA 89, 11920–11924 (1992); Gottlieb & Jackson, Cell 72, 131–142 (1993)). Under some assay conditions, DNA-PK that has been depleted of Ku protein can no longer be stimulated by double-stranded DNA (Dvir et al., J. Biol. Chem. 268, 10440–10447 (1993)).

Kinase Assay

Peptide phosphorylation was carried out using a previously described method (Lees-Miller et al., Mol. Cell. Biol. 12, 5041–5049 (1992)) with modifications. Reactions contained 1 riM Ku protein, 0.5 nM DNA-PKcs, 100 µM p53-derived peptide (EPPLSQEAFADLLWKK(SEQ ID NO:32), phosphorylation site underlined), 0.25 nM DNA fragment (308 base pair Bgl I-Blp I fragment from pHSE1 (Peterson et al., J. Biol. Chem. 270, 1449–1454 (1995b)), 4000 U/ml RNasin (Promega), 0.2 mM [g-$^{32}$P] ATP (1.25 Ci/mmol), 25 mM Tris-HCl, pH 7.9, 25 mM MgCl$_2$, 1.5 mM DTT, 50 mM KCl, and 10% glycerol in a total volume of 20 µl. Reactions were incubated at 30° C. for 45 minute, stopped by addition of 10 µl of 1 mg/ml BSA and 10 µl of 40% TCA, and further incubated for 30 minute on ice. Precipitated protein was removed by centrifugation and 10 µl of each supernatant, which contained the phosphorylated p53 peptide, was spotted on a phosphocellulose filter (Whatman P81). The filters were washed three times with 15% HOAc for 15 minutes, and incorporation of radiolabel was measured by liquid scintillation counting.

Ku-binding RNAs were able to block the ability of Ku protein to activate DNA-PK. Each of the nineteen selected aptamers, as well as the nonselected RNA pool, was tested in a DNA-PK assay. Each RNA was prepared by in vitro transcription and added to a DNA-PK phosphorylation assay.

Figure 2A:
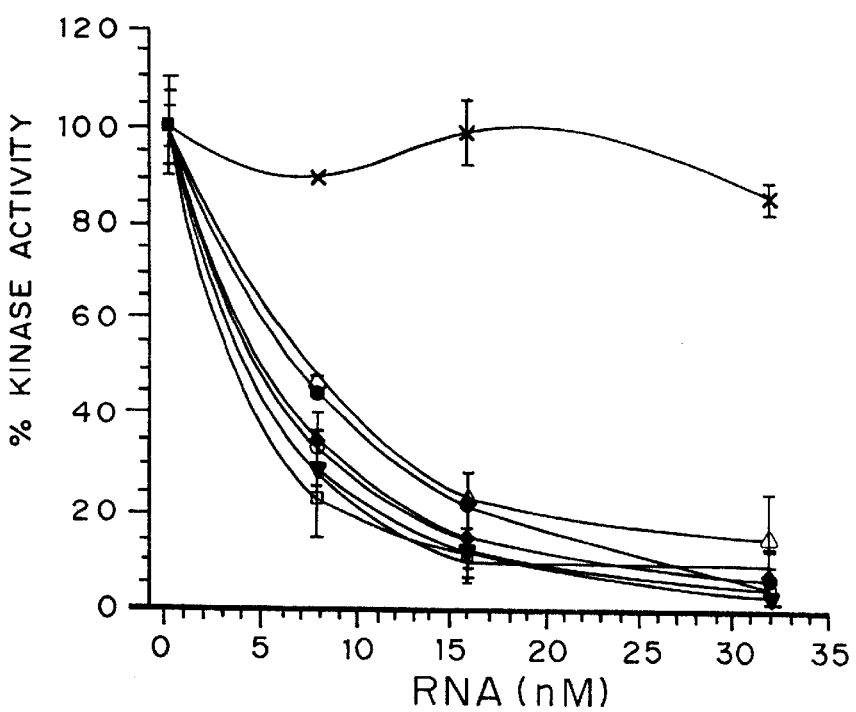
FIG. 2A is a graph of kinase activity (percentage of activity in absence of RNA) versus RNA concentration (nM) for eight representative aptamers. The aptamers were as follows: X, nonselected RNA; O, #2; □, #7-3; Δ, SC4; +, SC5; ♦, SC8; ▼, #1-2; ●, SC2.

DNA-PK assay reactions contained 0.5 nM Ku protein, 1 nM DNA-PKcs, 0.25 nM 308-base pair double-stranded DNA fragment, a synthetic peptide (EPPLSQEAFADLLWKK(SEQ ID NO:32)) containing a DNA-PK phosphorylation site from p53 (underlined), and the indicated amounts (8, 16, 32 nM) of RNA aptamer. Native DNA-PKcs were purified from HeLa cell nuclear extracts as described in example 2. In FIG. 2A, DNA-PK activity is expressed as a percentage of activity in the absence of RNA. Values shown are averages of duplicate reactions with standard deviations indicated. Background phosphorylation in the absence of DNA has been subtracted.

The effect on DNA-PK activity was measured, relative to control reactions with no added RNA. Nonselected RNA had no effect on DNA-PK activity (FIG. 2A). Of the selected RNAs, seven inhibited DNA-PK activity by 85% or more when present at 16–32 nM (FIG. 2A). Ten RNAs inhibited DNA-PK to a lesser extent and two had no effect on DNA-PK in the concentration range tested. These results indicate that at least some of the selected RNAs interact with regions of Ku protein that are critical for its biochemical activity. Since DNA-PKcs are known to have a low level of activity in the absence of Ku protein (Dvir et al., J. Biol. Chem. 268, 10440–10447 (1993)), the inhibition seen with the more effective RNAs probably reflects near-total ablation of Ku protein regulatory function.

RNAs Cannot Activate DNA-PK Directly

It was determined whether any of the RNAs were capable of activating, as opposed to inhibiting, DNA-PK phosphorylation activity. None of the RNAs significantly increased DNA-PK activity in a standard assay performed in the presence of DNA. However, under these conditions, the DNA-PK was already highly active and a weak ability of RNA to activate DNA-PK might have gone undetected. Indeed, displacement of DNA by a weakly activating RNA may have resulted in partial inhibition of DNA-PK activity.

To address the question whether any of the RNAs were capable of activating DNA-PK in the absence of DNA, DNA-PK assays in the absence of DNA were performed. Kinase assays were performed as described above in the presence or absence of 0.25 nM double-stranded DNA, as indicated. Reactions contained various amounts of aptamer RNA (8, 16, 32 nM).

When neither RNA nor DNA was present, DNA-PK had a low level of basal activity, as expected. The addition of double-stranded DNA increased this activity about ten-fold. Four RNAs were tested, including one that had given no effect on DNA-PK activity in the earlier assays (#52), two that had given partial inhibition (SC1, SC9), and one that had given potent inhibition (SC4). None of these four RNAs showed any ability to activate DNA-PK above background levels in the absence of DNA.

Competitive Binding Analysis Between Double Stranded DNA and RNA

In principle, an RNA that binds to Ku protein could inhibit DNA-PK either by blocking the binding of Ku protein to DNA or by blocking the interaction between Ku protein and DNA-PKcs. To distinguish these possibilities, the RNAs were tested for their effect on Ku protein-DNA binding.

Figure 2B:
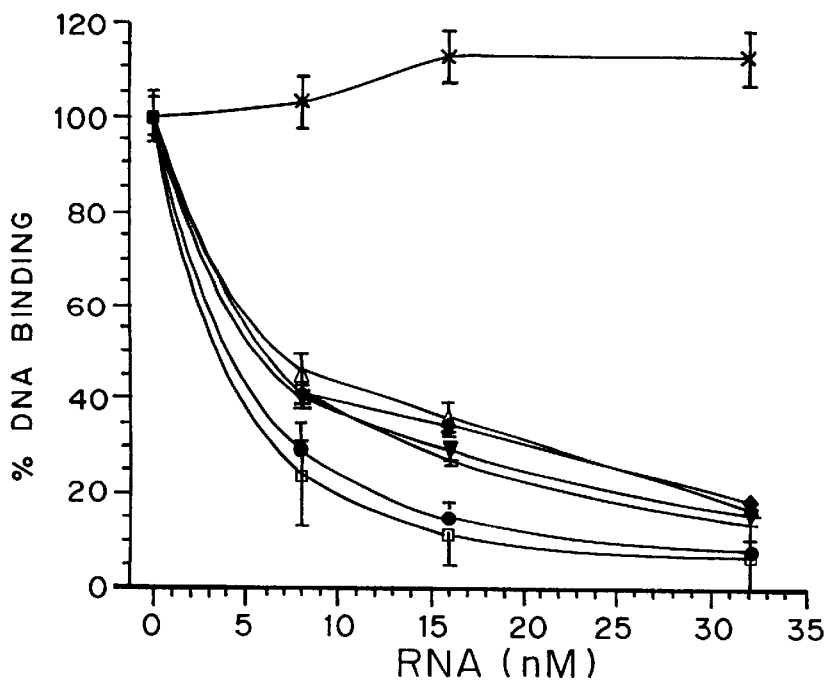
FIG. 2B is a graph of DNA binding (percent of Ku-DNA complexes detected in the absence of competitor) versus RNA concentration (nM) for seven representative aptamers. Purified Ku protein (2 nM) was incubated with radiolabeled 21 base pair double-stranded DNA (1 nM) in the presence of various amounts of nonselected RNA or aptamer. The aptamers were as follows: X, nonselected RNA; O, #2; □, #7-3; Δ, SC4; +, SC5; ♦, SC8; ▼, #1-2; ●, SC2.

Ku protein was incubated with a radiolabeled twenty-one base pair double stranded DNA (1 nM) oligonucleotide in the presence or absence of various amounts (8, 16, 32 nM) of nonradiolabeled RNA. The incubation conditions were 25 mM Tris-HCl pH 7.9, 0.5 mM EDTA, 10% glycerol, 5 mM $MgCl_2$, 0.5 mM DTT, 0.01% Tween, 120 mM KCl, 30 minute at ambient temperature. Ku protein-DNA complexes were trapped in a nitrocellulose filter binding assay as described in example 1 to measure Ku-DNA complexes. The results are shown in FIG. 2B, where binding is expressed as a percentage of Ku-DNA complexes detected in the absence of competitor. Values shown are averages of duplicate reactions with standard deviations indicated. Eleven cloned RNAs were tested, all of which had previously been shown to inhibit DNA-PK in a phosphorylation assay. All of these RNAs competed to some extent with the double-stranded DNA oligonucleotide for binding to Ku protein. The seven RNAs that functioned as effective inhibitors of DNA-PK enzyme activity also proved to be effective inhibitors of Ku protein-DNA binding activity (FIG. 2B). By contrast, RNA from the nonselected pool had no effect on Ku protein-DNA interaction (FIG. 2B). There was a rough correlation between the efficiency with which individual RNAs inhibited DNA binding and DNA-PK phosphorylation. Although not wishing to be bound by theory, the results suggest that all of the inhibitory RNAs that were tested work primarily by interfering with protein-DNA interactions, rather than protein-protein interactions.

Both of the subunits of Ku protein have a predicted net negative charge at neutral pH, and it may be that unfavorable electrostatic interactions restrict interaction with aptamer RNAs over much of the protein's surface. Given this constraint, it is perhaps not surprising that many of the aptamers are targeted toward the DNA binding site within the Ku protein. Although this site has not been fully mapped, it is likely that it contains basic residues that are capable of electrostatic interactions with the phosphate backbone of RNA and DNA.

To further explore the relationship between RNA and DNA binding sites in Ku protein, Electrophoretic Mobility Shift Assays (EMSAs) were performed comparing radiolabeled aptamer RNA (1 nM) and radiolabeled twenty-one base pair double stranded DNA (1 nM) probes. Cross-competition between RNA aptamers and DNA for Ku protein binding were found. It was discovered that Ku protein forms stable complexes with both types of probes, and that the complexes with RNA and DNA have similar electrophoretic mobilities. Both of the RNAs that were tested, #7-3 and #SC9, competed with DNA for binding to Ku protein. RNA #7-3 is a more effective competitor than RNA #SC9, consistent with the results of nitrocellulose filter binding assays. In the reciprocal experiment, nonradiolabeled DNA fragments competed with labeled RNA for binding to Ku protein. As controls, DNA and each RNA were shown to effectively self-compete for binding to Ku protein, confirming the fidelity of the analysis.

Notably, neither the DNA nor the RNA competitors induced the formation of supershifted complexes. The absence of supershifted complexes provides additional evidence that RNA and DNA cannot bind simultaneously to Ku protein, but rather, bind competitively to the same site.

Specific Inhibition of DNA-PK by Aptamers in Crude Cell Extracts

Part of the rationale for identifying RNAs that interact with Ku protein was to develop potential tools, aptamers, for in vivo modulation of DNA-PK activity. To be useful, such aptamers must not only recognize Ku protein, but they must be able to do so in a complex milieu containing other macromolecules.

Figure 3:
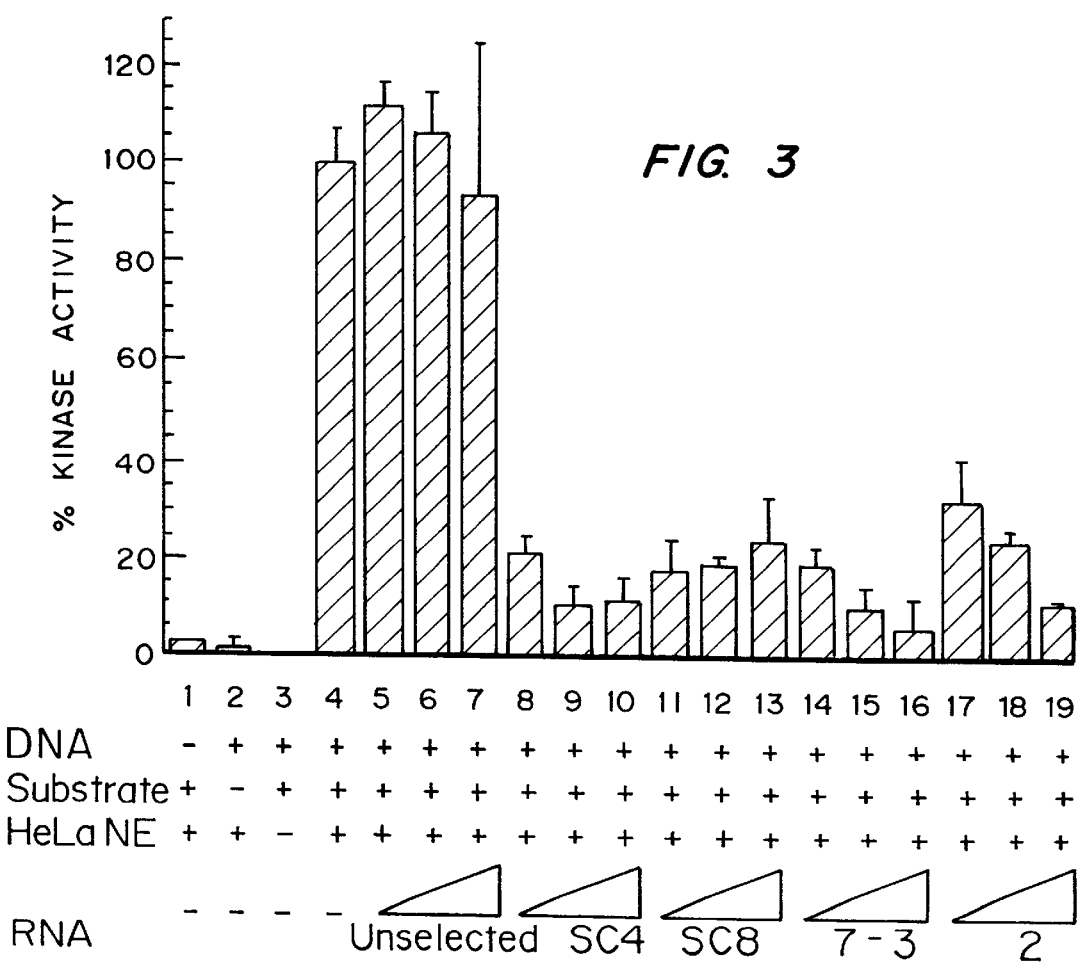
FIG. 3 is a bar graph of kinase activity (percentage of activity in the absence of RNA) in the presence of different aptamers, each at three different concentrations. Reactions were performed in crude nuclear extract. Reactions contained 2 μl HeLa cell nuclear extract (0.4 μg protein), substrate (Ku protein (2 nM)) and DNA (1 nM) were as in FIG. 2. Reactions were performed in the presence of various amounts of aptamer (250, 500, 1000 nM).
Figure 5:
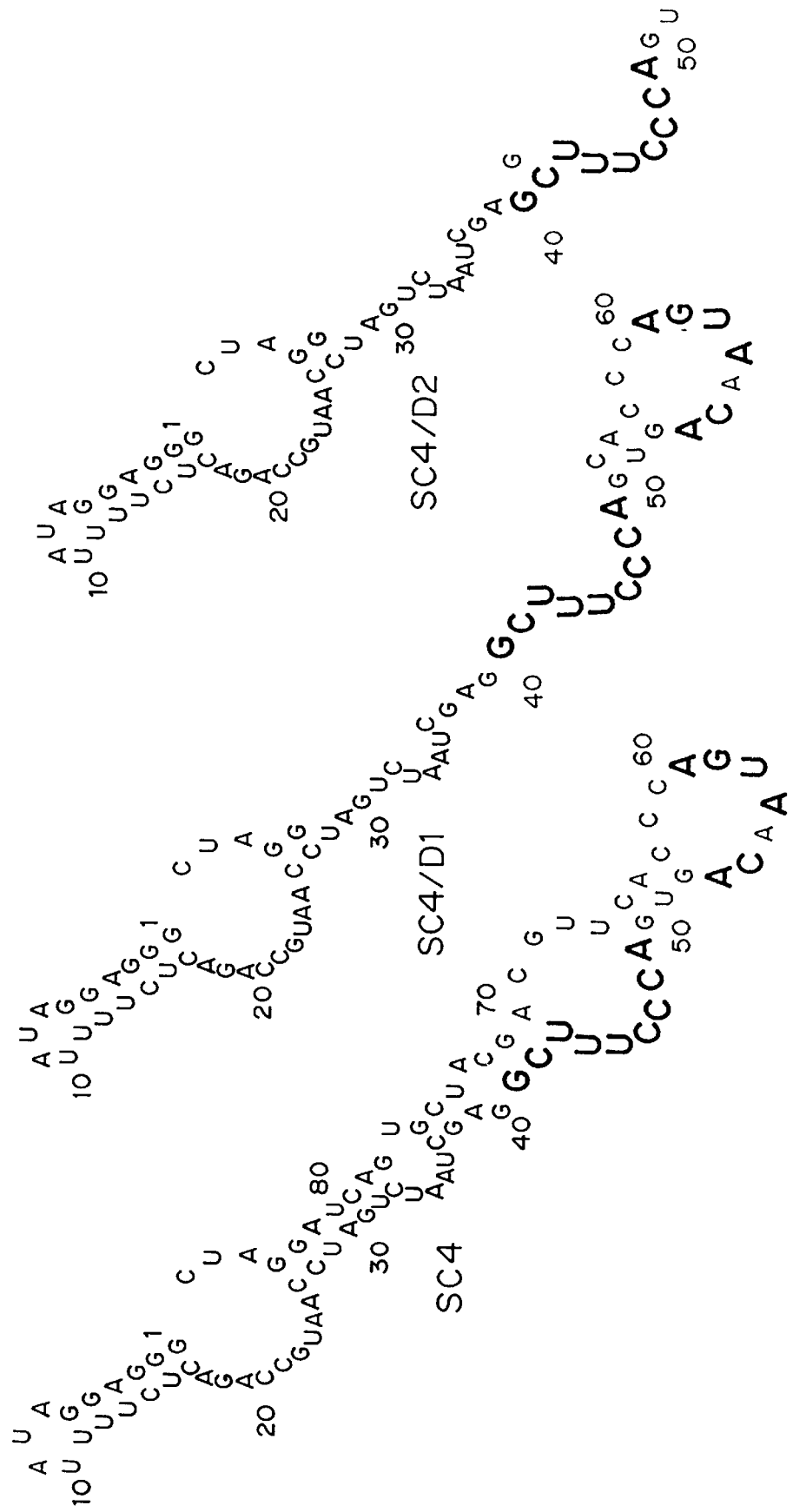
FIG. 5 shows the predicted secondary structure of the aptamer SC4 and the predicted secondary structure of the mutated aptamers, SC4/D1 and SC4/D2. The SC4 sequence depicted consists of the sequences, '5 to '3, of SEQ ID NOs: 22, 6, and 23: SC4/D1 is deleted for the 18 bases corresponding to positions 1–18 of SEQ ID NO: 23, relative to SC4: SC4/D2 is deleted for an additional 13 bases corresponding to positions 27–39 of SEQ ID NO: 6, relative to SC4/D1.

To determine whether the RNAs were specific for Ku protein, the ability of the aptamers to inhibit DNA-PK in crude HeLa cell nuclear extracts were measured. As shown in FIG. 3, phosphorylation of the p53-derived peptide substrate by crude extracts is stimulated at least five-fold by addition of double stranded DNA. This suggests that DNA-PK is the major kinase that phosphorylates this substrate under the conditions used. The reactions contained 2 $\mu$l HeLa cell nuclear extract (0.4 $\mu$g protein) and other components as in FIG. 2. Reactions were performed in the presence of various amounts of aptamer RNA (250, 500, 1000 nM) as indicated. The assays were as described 20 above except a higher amount of DNA was used, 5.3 nM. 100 to 142.1 $\mu$M p53 was used. DNA-PK activity is expressed as a percentage of activity in the absence of RNA. Values shown are averages of duplicate reactions with standard deviations as indicated. Four different aptamer RNAs, all of which had previously been shown to inhibit purified DNA-PK, were tested in the crude extract. All four reduced enzyme activity to near-basal levels. RNA from the nonselected pool had no effect at concentrations up to 1000 nM (FIG. 3, lanes 5–7). These results demonstrate that the aptamers are sufficiently selective that they can recognize Ku protein and inhibit DNA-PK activity even in a crude preparation.

Dissociation of Ku-DNA Complexes by Aptamer RNAs

Previous work has suggested that, once the Ku protein binds to double-stranded DNA, the resulting complexes are not readily disrupted by a second DNA added as competitor, except when the first and second DNAs have cohesive ends (Bliss & Lane, J. Biol. Chem. 272, 5765–5773 (1997)). To find out whether aptamers were capable of capturing Ku protein from preformed complexes, an experiment was performed in which purified Ku protein (0.32 nM) was incubated with a radiolabeled double-stranded DNA (5' end labelled with T-4 polynucleotide kinase and [$\gamma$-32P] ATP)

fragment (0.38 nM) under conditions for forming complexes for 30 minutes at room temperature. The complexes were challenged with either aptamer RNA or RNA from the nonselected pool. Incubation was then continued and the amount of Ku-DNA complexes remaining were measured by electrophoretic mobility assay using a 5% nondenaturing polyacrylamide gel containing 25 mM Tris-HCl pH 8.3, 190 mM glycine, 1 mM EDTA, run for one hour at 300 V, ambient temperature.

Ku protein-DNA complexes steadily dissociated in the presence of aptamer #7-3. In contrast, the amount of Ku protein-DNA complexes remained almost unchanged when challenged with nonselected RNA. This result demonstrates that the aptamer RNA can compete with double-stranded DNA for the binding of Ku protein even if the aptamer RNA is added after Ku-DNA complexes have formed.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a ", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. An oligomer comprising the sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and SEQ ID NO:19.

2. An oligomer comprising the sequence of SEQ ID NO: 2.

3. An oligomer comprising the sequence of SEQ ID NO: 5.

4. An oligomer comprising the sequence of SEQ ID NO: 6.

5. An oligomer comprising the sequence of SEQ ID NO: 7.

6. An oligomer comprising the sequence of SEQ ID NO: 9.

7. An oligomer comprising the sequence of SEQ ID NO: 15.

8. An oligomer comprising the sequence of SEQ ID NO: 17.

* * * * *

UNITED STATES PATENT AND TRADEMARK OFFICE
CERTIFICATE OF CORRECTION

PATENT NO.    : 6,441,158 B1
DATED         : August 27, 2002
INVENTOR(S)   : William S. Dynan and Sunghan Yoo It is certified that error appears in the above-identified patent and that said Letters Patent is hereby corrected as shown below:

Title page,
Item [56], OTHER PUBLICATIONS, in the reference beginning "Cary, et al.," please correct the word "an" to read -- and --

Column 6,
Line 7, please correct "SEQ ID NO: 21" to read -- SEQ ID NO: 23 --

Column 14,
Line 40, please correct "etal.," to read -- et al., --

Column 15,
Line 50, please correct the word "MRNA" to read -- mRNA --

Column 17,
Line 35, please correct the word "*NucleicAcids*" to read -- *Nucleic Acids* --

Column 24,
Lines 24 - 27, please delete the periods after the Celsius symbols to read
-- "amplification (93º C for 30 s, 57º C for 20 s, 73º C for 90 s), the reaction was extracted with an equal volume of phenol-chloroformisoamyl alcohol (25:24:1 *v/v/v*) (PCIA), and nucleic acids --
Lines 30 and 31, please delete the period after the Celsius symbol to read -- 37º C --
Line 41, please delete the period after the Celsius symbol to read -- 4º C --
Line 43, please delete the period after the Celsius symbol to read -- 100º C --
Line 45, please delete the period after the Celsius symbol to read -- 0º C --

Signed and Sealed this

Thirteenth Day of May, 2003

JAMES E. ROGAN
*Director of the United States Patent and Trademark Office*

SEQUENCE LISTING

```
<160> NUMBER OF SEQ ID NOS: 32

<210> SEQ ID NO 1
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer SC6

<400> SEQUENCE: 1
gacucacgau ggaccauacg ccuucccacu ggucuuguua                    40

<210> SEQ ID NO 2
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer #1-2

<400> SEQUENCE: 2
caacaccuug cuuucccaau acccugaaau acagucggau                    40

<210> SEQ ID NO 3
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
```

<223> OTHER INFORMATION: oligomer #1-17

<400> SEQUENCE: 3
uccuuauuuu auggcuuucc cacgcacaca agcgucugcg                    40

<210> SEQ ID NO 4
<211> LENGTH: 39
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(39)
<223> OTHER INFORMATION: oligomer #85

<400> SEQUENCE: 4
caaguaucac gcacuuuccc auucacuguu agagacuga                     39

<210> SEQ ID NO 5
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer #2

<400> SEQUENCE: 5
gccuaugcac ggagcuuucc cagcuacaga ugaaaccagc                    40

<210> SEQ ID NO 6
<211> LENGTH: 39
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(39)
<223> OTHER INFORMATION: oligomer SC4

<400> SEQUENCE: 6 ccuagcuaa ucgaggcuuu cccagugaca augacccac                      39

<210> SEQ ID NO 7
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer SC5

<400> SEQUENCE: 7
cuugaacaug auaggcuuac ccauagacag auugacccuu                    40

<210> SEQ ID NO 8
<211> LENGTH: 39
<212> TYPE: RNA
<213> ORGANISM: Artificial Sequence

```
<220> FEATURE:
<223> OTHER INFORMATION: Description of Artificial Sequence:
      oligonucleotide
<220> FEATURE:
<221> NAME/KEY: misc_RNA
<222> LOCATION: (1)..(39)
<223> OTHER INFORMATION: oligomer SC9

<400> SEQUENCE: 8
ugccuuuagc ugcgacaaug aacagcauga ccucacuac                               39

<210> SEQ ID NO 9
<211> LENGTH: 40
<212> TYPE: RNA
<213> ORGANISM: Artificial Sequence
<220> FEATURE:
<221> NAME/KEY: misc_RNA
<222> LOCATION: (1)..(40)
<223> OTHER INFORMATION: oligomer SC8
<220> FEATURE:
<223> OTHER INFORMATION: Description of Artificial Sequence:
      oligonucleotide

<400> SEQUENCE: 9
guccuucacu aaugcuuacc agacacacua agaacgucac                              40

<210> SEQ ID NO 10
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer SC3

<400> SEQUENCE: 10
cauuaccaca guucuagcau cccgcaaugg uaaguccgca                              40

<210> SEQ ID NO 11
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer SC1

<400> SEQUENCE: 11
uuguucaacc uugucuaaca ugauaccgau acggacuaca                              40

<210> SEQ ID NO 12
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer #84

<400> SEQUENCE: 12
auccgcguac cgggcucaaa ugucacuaua guagaaagca                              40
```

<210> SEQ ID NO 13
<211> LENGTH: 39
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(39)
<223> OTHER INFORMATION: oligomer #52

<400> SEQUENCE: 13
cugaucguuc aaugacuauu cuuuaccuug aguaaccga                    39

<210> SEQ ID NO 14
<211> LENGTH: 39
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(39)
<223> OTHER INFORMATION: oligomer SC12

<400> SEQUENCE: 14
cucgcaacau gacuucgaaa guuuaaucgu ucuugucaa                    39

<210> SEQ ID NO 15
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer #7-3

<400> SEQUENCE: 15
aggucggcau acagaguucc gaaugcgcgu aacuucgacu                   40

<210> SEQ ID NO 16
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer SC11

<400> SEQUENCE: 16
cuuaguuucg aucgaagcuc auuggcccag cguggauaac                   40

<210> SEQ ID NO 17
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer SC2

<400> SEQUENCE: 17
cacgcucuac aacagauugc gaauuaacuu acgcuucaua                    40

<210> SEQ ID NO 18
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer #42

<400> SEQUENCE: 18
cauccuggua cucacuucga caucguacgu ucaaucauac                    40

<210> SEQ ID NO 19
<211> LENGTH: 40
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(40)
<223> OTHER INFORMATION: oligomer SC13

<400> SEQUENCE: 19
accuuuuuag acgaaccuca aaguacauuu aguugaaaac                    40

<210> SEQ ID NO 20
<211> LENGTH: 14
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(14)
<223> OTHER INFORMATION: aptamer motif 1

<400> SEQUENCE: 20
gcuuucccan nnac                                                14

<210> SEQ ID NO 21
<211> LENGTH: 6
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(6)
<223> OTHER INFORMATION: aptamer motif 2

<400> SEQUENCE: 21 amauga                                                          6

<210> SEQ ID NO 22
<211> LENGTH: 25
<212> TYPE: RNA

```
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(25)
<223> OTHER INFORMATION: sequence that is 5' to sequences SEQ ID NO:1
      through SEQ ID NO:19

<400> SEQUENCE: 22
gggaggauau uuucucagac cguaa                                          25

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(23)
<223> OTHER INFORMATION: sequence that is 3' to sequences SEQ ID NO:1
      through SEQ ID NO:19

<400> SEQUENCE: 23
uugcagcauc gugaacuagg auc                                            23

<210> SEQ ID NO 24
<211> LENGTH: 12
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(12)
<223> OTHER INFORMATION: sequence possibly contained in Component D of
      sequences SEQ ID NO:1 through SEQ ID NO:19

<400> SEQUENCE: 24
acnnaugann nn                                                        12

<210> SEQ ID NO 25
<211> LENGTH: 11
<212> TYPE: RNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_RNA
<222> LOCATION: (1)..(11)
<223> OTHER INFORMATION: sequence possibly contained in Component D of
      sequences of SEQ ID NO:1 through SEQ ID NO:19

<400> SEQUENCE: 25
acmaugannn n                                                         11

<210> SEQ ID NO 26
<211> LENGTH: 12
<212> TYPE: RNA
<213> ORGANISM: Artificial Sequence
<220> FEATURE:
<223> OTHER INFORMATION: Description of Artificial Sequence:
      oligonucleotide

<400> SEQUENCE: 26
```
acagaugaaa cc    12

<210> SEQ ID NO 27
<211> LENGTH: 92
<212> TYPE: DNA
<213> ORGANISM: Artificial Sequence
<220> FEATURE:
<223> OTHER INFORMATION: Description of Artificial Sequence:
    oligonucleotide
<220> FEATURE:
<221> NAME/KEY: misc_feature
<222> LOCATION: (1)..(92)
<223> OTHER INFORMATION: template for RNA synthesis

<400> SEQUENCE: 27
cccggatcct agttcacgat gctgcaannn nnnnnnnnnn nnnnnnnnnn nnnnnnnnnn    60
nnnnnnntta cggtctgaga aaatatcctc cc    92

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence:
    oligonucleotide
<220> FEATURE:
<221> NAME/KEY: misc_feature
<222> LOCATION: (1)..(50)
<223> OTHER INFORMATION: primer 1

<400> SEQUENCE: 28
cccaagctta atacgactca ctatagggag gatattttct cagaccgtaa    50

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence:
    oligonucleotide
<220> FEATURE:
<221> NAME/KEY: misc_feature
<222> LOCATION: (1)..(27)
<223> OTHER INFORMATION: primer 2

<400> SEQUENCE: 29
cccggatcct agttcacgat gctgcaa    27

<210> SEQ ID NO 30
<211> LENGTH: 21
<212> TYPE: DNA
<213> ORGANISM: Homo sapiens
<220> FEATURE:
<221> NAME/KEY: promoter
<222> LOCATION: (1)..(21)
<223> OTHER INFORMATION: Human T-cell leukemia virus proviral promoter

<400> SEQUENCE: 30
ctcaggcgtt gacgacaacc c    21

<210> SEQ ID NO 31
<211> LENGTH: 59
<212> TYPE: RNA
<213> ORGANISM: Artificial Sequence
<220> FEATURE:
<223> OTHER INFORMATION: Description of Artificial Sequence:
    oligonucleotide
<220> FEATURE:
<221> NAME/KEY: misc_feature

```
<222> LOCATION: (1)..(59)
<223> OTHER INFORMATION: sequence derived from HIV

<400> SEQUENCE: 31
gggucucucu gguuagacca gaucugagcc ugggagcucu cuggcuaacu agggaaccc      59

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: PEPTIDE
<222> LOCATION: (1)..(16)
<220> FEATURE:
<221> NAME/KEY: SITE
<222> LOCATION: (5)
<223> OTHER INFORMATION: DNA-PK phosphorylation site from p53

<400> SEQUENCE: 32

Glu Pro Pro Leu Ser Gln Glu Ala Phe Ala Asp Leu Leu Trp Lys Lys
  1               5                  10                  15
```